United States Patent [19]

Steuerle et al.

[11] Patent Number: 6,056,967
[45] Date of Patent: May 2, 2000

[54] METHOD OF PRODUCING WATER-SOLUBLE CONDENSATES AND ADDITION PRODUCTS CONTAINING AMINO GROUPS, AND USE OF SAID CONDENSATES AND ADDITION PRODUCTS

[75] Inventors: Ulrich Steuerle, Heidelberg; Hubert Meixner, Ludwigshafen; Rainer Dyllick-Brenzinger, Weinheim; Wolfgang Reuther, Heidelberg; Hartmut Kanter, Weisenheim a. Sand; Albert Hettche, Hessheim; Jürgen Weiser, Schriesheim; Günter Scherr, Ludwigshafen, all of Germany

[73] Assignee: BASF Aktiengesellschaft, Ludwigshafen, Germany

[21] Appl. No.: 09/101,184

[22] PCT Filed: Jan. 3, 1997

[86] PCT No.: PCT/EP97/00009

§ 371 Date: Jul. 6, 1998

§ 102(e) Date: Jul. 6, 1998

[87] PCT Pub. No.: WO97/25367

PCT Pub. Date: Jul. 17, 1997

[30] Foreign Application Priority Data

Jan. 8, 1996 [DE] Germany .............. 196 00 366
May 28, 1996 [DE] Germany .............. 196 21 300

[51] Int. Cl.$^7$ ............... A61K 7/00; A61K 7/06; C08F 6/00
[52] U.S. Cl. ........... 424/401; 424/70.1; 424/70.11; 162/100; 528/480; 528/502 A
[58] Field of Search ................. 528/310, 271, 528/272, 480, 502 A; 162/100; 424/401, 70.1, 70.11

[56] References Cited

U.S. PATENT DOCUMENTS

| 2,182,306 | 12/1939 | Ulrich et al. . |
|---|---|---|
| 3,203,910 | 8/1965 | Wilson . |
| 3,893,885 | 7/1975 | Ziemann et al. . |
| 4,066,494 | 1/1978 | Scharf et al. . |
| 5,055,197 | 10/1991 | Albright et al. . |
| 5,536,370 | 7/1996 | Scherr et al. . |
| 5,641,855 | 6/1997 | Scherr et al. . |
| 5,677,384 | 10/1997 | Detering et al. . |

FOREIGN PATENT DOCUMENTS

| 0 411 400 | 2/1991 | European Pat. Off. . |
|---|---|---|
| 2 162 567 | 7/1972 | Germany . |
| 1 771 814 | 8/1972 | Germany . |
| 29 16 356 | 11/1980 | Germany . |
| WO 94/12560 | 6/1994 | WIPO . |
| WO 94/14873 | 7/1994 | WIPO . |

OTHER PUBLICATIONS

G. B. Guise, et al., Journal of Applied Polymer Science, vol. 30, pp. 4099 to 4111, "The Chemistry of a Polyamide–Epichlorohydrin Resin (Hercosett 125) Used to Shrink–Resist Wool", 1985.

*Primary Examiner*—Thurman K. Page
*Assistant Examiner*—Brian K. Seidleck
*Attorney, Agent, or Firm*—Oblon, Spivak, McClelland, Maier, & Neustadt, P.C.

[57] ABSTRACT

A process for the preparation of water-soluble, amino-containing condensates and adducts having a greater drainage and retention effect in papermaking, in which from 5 to 95% by weight of the condensates or adducts are separated off as permeate from solutions of water-soluble, amino-containing condensates or adducts by ultrafiltration through membranes and the amino-containing condensates or adducts having improved efficiency are, if required, isolated from the retentate, and the high molecular weight polymer fractions contained in the retentate are used as retention aids, drainage aids and fixing compositions in papermaking, as promoters in the sizing of paper with alkyldiketenes, as flocculants for sewage sludges, as adhesion promoters in the production of laminated films, as additives for hair and skincare compositions and as compositions for immobilizing anionic active ingredients.

11 Claims, No Drawings

METHOD OF PRODUCING WATER-SOLUBLE CONDENSATES AND ADDITION PRODUCTS CONTAINING AMINO GROUPS, AND USE OF SAID CONDENSATES AND ADDITION PRODUCTS

This application is a 371 of PCT/EP97/00009 filed Jan. 3, 1997.

The present invention relates to a process for the preparation of water-soluble, amino-containing condensates and adducts and their use as retention aids, drainage aids and fixing compositions in papermaking, as promoters in the sizing of paper with alkyldiketenes, as flocculants for sewage sludges, as adhesion promoters for the production of laminated films, as additives in hair and skincare compositions and as compositions for immobilizing anionic active ingredients.

Water-soluble amino-containing condensates or adducts have long been used as retention aids, drainage aids and fixing compositions in papermaking. For example, DE-B-1 771 814 discloses a method for increasing the retention of fibers, fillers and pigments in papermaking, for accelerating the drainage of paper stock suspensions and for working up paper machine waste waters. The process assistants used here are reaction products which are prepared by reacting water-soluble or water-dispersible basic polyamides as crosslinking agents which contain at least two functional groups which react with the amino groups of the basic polyamides. Such crosslinking agents are, for example, $\alpha,\omega$-alkyl dihalides, $\alpha,\omega$-dihaloethers, epichlorohydrin, $\omega$-halocarbonyl halides, bisglycidyl ethers, bisepoxides, divinyl ether, divinyl sulfone and methylenebisacrylamide.

Water-soluble amino-containing adducts are, for example, polyethyleneimines, which are usually prepared by polymerizing ethyleneimine in the presence of acids, Lewis acids or haloalkanes (cf. U.S. Pat. No. 2,182,306 and U.S. Pat. No. 3,203,910). Polyethyleneimines have likewise long been used as retention aids, drainage aids and fixing compositions in papermaking.

U.S. Pat. No. 4,144,123 (corresponds to DE-B-24 34 816) discloses a process for the preparation of nitrogen-containing condensates, in which polyamidoamines are grafted with ethyleneimine and the reaction products thus obtained are reacted with $\alpha,\omega$-bis(chlorohydrin) ethers of polyalkylene oxides at from 20 to 100° C., the reaction being carried out until the formation of high molecular weight resins which are still just water-soluble and have a viscosity of more than 300 mPa·s, measured at 20° C. in 20% strength by weight aqueous solution. The condensates thus obtained are likewise used as retention aids, flocculants and drainage aids in papermaking.

Further process assistants which are suitable for papermaking are reaction products of polyalkylenepolyamines or ethylenediamine with, for example, dichloroethane or other bifunctional or polyfunctional crosslinking agents. Such reaction products are disclosed, for example, in EP-A-0 411 400 and DE-A-2 162 567.

U.S. Pat. No. 4,066,494 discloses the use of nitrogen-containing condensates based on polyalkylenepolyamines as drainage accelerators and retention aids in the paper industry. The nitrogen-containing condensates are prepared by reacting polyalkylenepolyamines which contain from 15 to 500 alkyleneimine units with $\alpha,\omega$-chlorohydrin ethers of polyethylene oxides which contain from 18 to 90 ethylene oxide units at from 20 to 100° C. with formation of high molecular weight resins which are still water-soluble.

DE-C-2 916 356 discloses a process for the preparation of water-soluble polyetheramines, in which di- or polyamines having from 2 to 10 nitrogen atoms are first subjected to a condensation reaction with chlorohydrin ethers obtained from 1 mol of a dihydric alcohol of 2 to 5 carbon atoms, ethoxylation products thereof which contain up to 18 ethylene oxide units, glycerol or polyglycerol which contains up to 15 glycerol units, and at least from 2 to 8 mol of epichlorohydrin, in polar, water-miscible solvents in the absence of water or with substantial exclusion of water at from 110 to 200° C., and an alkali metal base or alkaline earth metal base is then added in an amount sufficient to neutralize at least 20% of the hydrogen chloride formed in the condensation. A Postcondensation is then also carried out. The condensates are used as flocculants, retention aids and drainage aids in papermaking.

WO-A-94/12560 discloses further water-soluble, amino-containing condensates which are obtainable by first partially amidating polyalkylenepolyamines, preferably polyethyleneimine, by reaction with, for example, monocarboxylic acids, and then reacting the resulting reaction products with bifunctional or polyfunctional crosslinking agents to give crosslinked polyalkylenepolyamines, which have a viscosity of at least 100 mPa·s in 20% strength by weight aqueous solution at 20° C. These polymers are likewise used as drainage aids, flocculants and retention aids and as fixing compositions in papermaking.

WO-A-94/14873 likewise discloses water-soluble, amino-containing polymers which are obtainable by reacting Michael adducts of, for example, polyalkylenepolyamines, polyamidoamines or ethyleneimine-grafted polyamidoamines and monoethylenically unsaturated carboxylic acids, salts, esters, amides or nitriles of monoethylenically unsaturated carboxylic acids with bifunctional or polyfunctional crosslinking agents to give water-soluble condensates, which have a viscosity of at least 100 mPa·s in 20% strength by weight aqueous solution at 20° C. The polymers are used as drainage aids, flocculants and retention aids in papermaking.

Journal of Applied Polymer Science, 30 (1985), 4099–4111 discloses that polyamidoamine/epichlorohydrin resins which are used for the antifelting treatment of wool (shrink-resist wool) or as wet strength agents in papermaking can be separated into a plurality of fractions by ultrafiltration. If two main fractions obtained in the ultrafiltration are tested for their efficiency in the antifelting treatment of wool, only small differences are found. For example, the properties of chlorinated wool treated in each case with one of the two fractions obtained in the ultrafiltration and with a nonfractionated sample of the polyamidoamine/epichlorohydrin resin are very similar. It is therefore concluded that a change of process in the preparation of such resins for increasing the proportion of a fraction is not associated with a practical advantage for the antifelting treatment of wool.

It is an object of the present invention to provide a process for the preparation of water-soluble, amino-containing condensates and adducts, the products obtained having greater efficiency in use than comparable prior art products, for example having a greater drainage and retention effect in papermaking.

We have found that this object is achieved, according to the invention, by a process for the preparation of water-soluble, amino-containing condensates and adducts having a greater drainage and retention effect in papermaking, if aqueous solutions of condensates or adducts selected from the group consisting of reaction products of alkylenediamines, polyalkylenepolyamines, ethyleneimine-grafted polyamidoamines and mixtures thereof with crosslinking agents having at least two functional groups, reaction products of Michael adducts of polyalkylene polyamines, polyamidoamines, ethyleneimine-grafted polyamidoamines and mixtures thereof and monoethylenically unsaturated carboxylic acids and salts, esters, amides or nitriles thereof with at least bifunctional crosslinking agents, amidated polyethyleneimines obtained by reaction of polyethyleneimines with monobasic carboxylic acids or their esters, anhydrides, acid chlorides or acid amides and, if required, reaction of the amidated polyethyleneimines with crosslinking agents having at least two functional groups, polyethyleneimines, quaternized polyethyleneimines, phosphonomethylated polyethyleneimines, alkoxylated polyethyleneimines and/or polyethyleneimines carboxymethylated by a Strecker reaction and crosslinked alkoxylated polyethyleneimines, crosslinked, quaternized polyethyleneimines, crosslinked, phosphonomethylated polyethyleneimines and/or crosslinked polyethyleneimines carboxymethylated by a Strecker reaction are subjected to an ultrafiltration through membranes, from 5 to 95% by weight of the condensates or adducts being separated off as permeate and the water-soluble, amino-containing condensates or adducts having improved efficiency, if required, isolated from the retentate.

All commercially available membranes which have a cut-off for polymers having molar masses of, for example, from 1000 to 10 million preferably from 1500 to 500,000, may be used for the ultrafiltration. Membranes having cut-offs for molar masses of from 3000 to 300,000 are particularly preferably used. The cut-off of the membranes used in each case should be adapted to the molecular weight distribution of the water-soluble amino-containing condensates or adducts, which are also referred to below as water-soluble polymers or as polymers for the sake of simplicity, so that it is possible to separate off from 5 to 95% by weight of polymer. In the ultrafiltration, the low molecular weight fractions of the polymers whose molar mass is below the cut-off are then separated off as permeate. The higher molecular weight fractions of polymer remain in the retentate. According to the present invention, the ultrafiltration also comprises microfiltration through membranes, membranes having a mean pore diameter of from 0.01 to 10 $\mu$m, preferably from 0.1 to 1 $\mu$m, being used. Separating off low molecular weight fractions gives amino-containing water-soluble condensates or adducts having a narrower molar mass distribution and an efficiency which is increased in an unforeseeable manner, for example when used as process assistants in papermaking.

The membranes may be used, for example, in the form of tubes, hollow fibers, sheet-type apparatuses or spiral-wound modules. Suitable materials for the membranes are, for example, regenerated cellulose, cellulose acetate, cellulose triacetate, polyamide, polyacrylonitrile, acrylonitrile copolymers, polysulfone, copolymers of vinyl chloride, polyimide, polyvinylidene fluoride, polytetrafluoroethylene, polymethyl methacrylate, hydrolyzed copolymers of ethylene and vinyl acetate, in which the vinyl acetate groups have a degree of hydrolysis of at least 50%, polycarbonate, polyethylene which is prepared from ethylene by the high pressure polymerization process at HDPE (polyethylene having a very high density), polypropylene, mineral or ceramic membranes or in particular mechanically stable membranes, such as metallic membranes, for example membranes of stainless steel which may be associated with a secondary membrane. The secondary membrane may consist of titanium oxide or zirconium oxide or of an organic material, such as polysulfone. Membranes based on polysulfone are preferably used. A review of ultrafiltration and membranes suitable for this purpose is given, for example, by Munir Cheryan in Ultrafiltration Handbook, Technomic Publishing Company, Inc., 1986.

Membranes which are suitable for the ultrafiltration are offered by many companies, cf. Catalog of the International Meeting on Chemical Technology and Biotechnology ACHEMA 94, Frankfurt am Main.

The ultrafiltration of the aqueous solutions of amino-containing polymers having a broad molar mass distribution is carried out in a conventional manner. It is preferably effected at room temperature, and aqueous solutions of polymers containing ethyleneimine units are used. The temperature of the aqueous polymer solutions may be, for example, from 10 to 80° C. The ultrafiltration can be carried out under atmospheric pressure or under superatmospheric pressure on the retentate side, for example at from 1.5 to 50, preferably from 2 to 20, bar. The pH of the aqueous solutions of amino-containing polymers is, for example, from 2 to 14, preferably from 4 to 12, and in particular from 8 to 12, during the ultrafiltration.

The ultrafiltration of the water-soluble, amino-containing polymers which have a broad molar mass distribution is carried out by separating off from 5 to 95, preferably from 20 to 90, %, by weight, based on the polymers used, of polymers as permeate and, if necessary, isolating the polymers having a higher molar mass and surprisingly improved quality from the retentate. The amount of low molecular weight polymer separated off as permeate is in general from 30 to 70% by weight.

It has been found that the water-soluble, amino-containing condensates and adducts employed in the process according to the invention have a broad molar mass distribution $M_w/M_n$. For example, ethyleneamine-grafted, crosslinked polyamidoamines have a molar mass distribution $M_w/M_n$ of 400. The molar mass distribution is determined by gel permeation chromatography, based on Pullulan standards with water as eluent. The retentates prepared according to the invention have, for example, viscosities of from 120 to 5000, preferably from 200 to 1500, mPa·s (measured in a Brookfield viscometer using 10% strength by weight polymer solutions at 20° C. and pH 10) and a molar mass distribution $M_w/M_n$ of, for example, from 2 to 350, preferably from 10 to 300.

In the novel process, all water-soluble, amino-containing polymers which usually have a broad molar mass distribution can be separated into polymers having a narrower distribution and high molecular weight fractions and into polymers having low molecular weight fractions. Amino-containing polymers are known. They were essentially described above as prior art. These are, for example, reaction products of alkylenediamines or polyalkylenepolyamines with crosslinking agents containing at least two functional groups.

This group also includes ethylene-imine-grafted polyamidoamines, which are described in U.S. Pat. No. 4,144,123 stated in connection with the prior art. The polyamidoamines are prepared, for example, by reacting dicarboxylic acids of 4 to 10 carbon atoms with polyalkylenepolyamines which preferably contain from 3 to 10 basic nitrogen atoms in the molecule. Suitable dicarboxylic acids are, for example, succinic acid, maleic acid, adipic acid, glutaric acid, suberic acid, sebacic acid and terephthalic acid. Mixtures of adipic acid and glutaric acid or maleic acid and adipic acid may also be used. Adipic acid is preferably used for the preparation of the polyamidoamines.

Suitable polyalkylenepolyamines which are subjected to condensation reaction with the dicarboxylic acids are, for example, diethylenetriamine, triethylenetetramine, dipropylenetriamine, tripropylenetetramine, dihexamethylenetriamine, aminopropylethylenediamine and bisaminopropylethylenediamine. The polyalkylenepolyamines may also be used in the form of mixtures in the preparation of the polyamidoamines. The polyamidoamines are preferably prepared by condensation of dicarboxylic acids and polyamines in the absence of a solvent. However, the condensation may, if required, also be carried out in inert solvents. The condensation of the dicarboxylic acids with the polyalkylenepolyamines is usually carried out at, for example, from 100 to 220° C., the water formed in the reaction being distilled off from the reaction mixture. The condensation can, if required, additionally be carried out in the presence of lactones or lactams of carboxylic acids of 4 to 8 carbon atoms, for example in the presence of caprolactam. For example, from 0.8 to 1.4 mol of a polyalkylenepolyamine are used per mol of a dicarboxylic acid. The polyamidoamines thus obtainable have primary and secondary NH groups and may also have tertiary nitrogen atoms and are soluble in water.

The polyamidoamines described above are grafted with ethyleneimine by, for example, allowing ethyleneimine to act on the polyamidoamines in the presence of acids (eg. sulfuric acid or phosphoric acid) or in the presence of Lewis acids (eg. boron trifluoride etherates). For example, from 1 to 50, preferably from 2 to 25, ethyleneimine units may be grafted on per basic nitrogen group in the polyamidoamine, ie., for example, from about 10 to 500 parts by weight of ethyleneimine are used per 100 parts by weight of a polyamidoamine. These reaction products may be subjected to ultrafiltration, although preferred reaction products are those which can be prepared by grafting of polyamidoamines with ethyleneimine and subsequent reaction of the grafted products with crosslinking agents containing at least two functional groups. products of this type are used, for example according to the above-mentioned U.S. Pat. No. 4,144,123, as retention aids, flocculants and drainage aids in papermaking. Examples of suitable crosslinking agents are bischlorohydrin ethers or bisglycidyl ethers of polyalkylene glycols, which contain from 8 to 100, preferably 15–50, alkylene oxide units. For the preparation of the water-soluble amino-containing condensates, for example, one part by weight of an ethyleneimine-grafted polyamidoamine is reacted with from 0.3 to 2 parts by weight of the bisglycidyl ethers or of the other crosslinking agents having at least two functional groups. Particularly preferably used condensates are reaction products which are obtainable by crosslinking ethyleneimine-grafted polyamidoamines with bisglycidyl ethers of polyalkylene glycols which contain from 8 to 100 ethylene oxide and/or propylene oxide units.

In addition to the bischlorohydrin or glycidyl ethers of polyalkylene glycols as crosslinking agents containing at least two functional groups, which bischlorohydrin or glycidyl ethers are described in U.S. Pat. No. 4,144,123, $\alpha,\omega$-dichloropolyalkylene glycols which are disclosed, for example, as crosslinking agents in EP-B-0 025 515 are suitable. They are obtainable by a method in which dihydric to tetrahydric alcohols, preferably alkoxylated dihydric to tetrahydric alcohols, either are reacted with thionyl chloride with elimination of HCl and subsequent catalytic decomposition of the chlorosulfonated compounds with elimination of sulfur dioxide or they are converted with phosgene into the corresponding bischlorocarbonic esters with elimination of HCl and $\alpha,\omega$-dichloroethers are then obtained therefrom by catalytic decomposition with elimination of carbon dioxide. Preferably used alcohol components are ethoxylated and/or propoxylated glycols, which are reacted with from 1 to 100, in particular from 4 to 40, mol of ethylene oxide per mol of glycol.

Other suitable crosslinking agents are $\alpha,\omega$-dichloroalkanes or vicinal dichloroalkanes, for example 1,2-dichloroethane, 1,2-dichloropropane, 1,3-dichloropropane, 1,4-dichlorobutane and 1,6-dichlorohexane. Examples of further crosslinking agents are the reaction products of at least trihydric alcohols with epichlorohydrin to give reaction products which have at least two chlorohydrin units; for example glycerol, ethoxylated or propoxylated glycerols, polyglycerols having from 2 to 15 glycerol units in the molecule and polyglycerols which may be ethoxylated and/or propoxylated are used as polyhydric alcohols. Crosslinking agents of this type are disclosed, for example, in DE-A-2 916 356. Crosslinking agents which contain blocked isocyanate groups, for example trimethylhexamethylene diisocyanate blocked with 2,2,3,6-tetramethylpiperidin-4-one, are also suitable. Such crosslinking agents are known (cf. for example DE-A-4 028 285), as well as crosslinking agents containing aziridine units and based on polyethers or substituted hydrocarbons, eg. 1,6-bis-N-aziridinohexane (cf. U.S. Pat. No. 3,977,923). It is of course also possible to use mixtures of two or more crosslinking agents for increasing the molecular weight.

In papermaking, particularly preferred process assistants are those which are free of organically bonded halogen. Halogen-free crosslinking agents are therefore used for the preparation of amino-containing condensates or amino-containing adducts, each of which is soluble in water. The halogen-free crosslinking agents are bifunctional or polyfunctional and are preferably selected from the group consisting of:

(1) ethylene carbonate, propylene carbonate and/or urea, (2) monoethylenically unsaturated carboxylic acids and esters, amides and anhydrides thereof, at least dibasic saturated carboxylic acids or polycarboxylic acids and the esters, amides and anhydrides derived from each of them, (3) reaction products of polyetherdiamines, alkylenediamines, polyalkylenepolyamines, alkylene glycols, polyalkylene glycols or mixtures thereof with monoethylenically unsaturated carboxylic acids, esters, amides or anhydrides of monoethylenically unsaturated carboxylic acids, the reaction products having at least two ethylenically unsaturated double bonds, and carboxamido, carboxyl or ester groups as functional groups, (4) reaction products of dicarboxylic esters with ethyleneimine, which reaction products contain at least two aziridino groups, and mixtures of the stated crosslinking agents.

Suitable crosslinking agents of the group (1) are ethylene carbonate, propylene carbonate and urea. From this group of monomers, propylene carbonate is preferbly used. The crosslinking agents of this group react to give amino-containing urea compounds.

Suitable halogen-free crosslinking agents of the group (2) are, for example, monoethylenically unsaturated monocarboxylic acids, such as acrylic acid, methacrylic acid and crotonic acid, and the amides, esters and anhydrides derived therefrom. The esters may be derived from alcohols of 1 to 22, preferably of 1 to 18, carbon atoms. The amides are preferably unsubstituted but may carry a $C_1$–$C_{22}$-alkyl radical as a substituent.

Further halogen-free crosslinking agents of the group (2) are at least dibasic saturated carboxylic acids, such as dicarboxylic acids, and salts, diesters and diamides derived therefrom. These compounds may be characterized, for example, with the aid of the formula

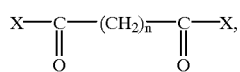 (I)

where

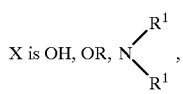

R is $C_1$–$C_{22}$-alkyl,
$R^1$ is H or $C_1$–$C_{22}$-alkyl and
n is from 0 [sic] to 22

In addition to the dicarboxylic acids of the formula I, for example, monoethylenically unsaturated dicarboxylic acids, such as maleic acid or itaconic acid, are suitable. The esters of the suitable dicarboxylic acids are preferably derived from alcohols of 1 to 4 carbon atoms. Examples of suitable dicarboxylic esters are dimethyl oxalate, diethyl oxalate, diisopropyl oxalate, dimethyl succinate, diethyl succinate, diisopropyl succinate, di-n-propyl succinate, diisobutyl succinate, dimethyl adipate, diethyl adipate and diisopropyl adipate. Suitable esters of ethylenically unsaturated dicarboxylic acids are, for example, dimethyl maleate, diethyl maleate, diisopropyl maleate, dimethyl itaconate and diisopropyl itaconate. Substituted dicarboxylic acids and their esters, such as tartaric acid (D and L forms and racemate) and tartaric esters, such as dimethyl tartrate and diethyl tartrate, are also suitable.

Examples of suitable dicarboxylic anhydrides are maleic anhydride, itaconic anhydride and succinic anhydride. The crosslinking of amino-containing compounds of component (a) with the abovementioned halogen-free crosslinking agents takes place with formatio of amido groups or, in the case of amides, such as adipamide, by transamidation. Maleic esters, monoethylenically unsaturated dicarboxylic acids and anhydrides thereof can effect crosslinking both by formation of carboxamido groups and by a Michael addition reaction of NH groups of the components to be crosslinked (for example of polyamidoamines).

At least dibasic saturated carboxylic acids include, for example, tri- and tetracarboxylic acids, such as citric acid, propanetricarboxylic acid, ethylenediaminetetraacetic acid and butanetetracarboxylic acid. other suitable crosslinking agents of group (2) are polycarboxylic acids, which are obtainable by polymerizing monoethylenically unsaturated carboxylic acids or anhydrides.

Other suitable crosslinking agents of the group (2) are polycarboxylic acids which are obtainable by polymerizing monoethylenically unsaturated carboxylic acids or anhydrides. Examples of suitable monoethylenically unsaturated carboxylic acids are acrylic acid, methacrylic acid, fumaric acid, maleic acid and/or itaconic acid. Thus, suitable crosslinking agents are, for example, polyacrylic acids, copolymers of acrylic acid and methacrylic acid and copolymers of acrylic acid and maleic acid.

Further suitable crosslinking agents (2) are prepared, for example, by polymerizing anhydrides, such as maleic anhydride, in an inert solvent, such as toluene, xylene, ethylbenzene or isopropylbenzene, or a solvent mixture in the presence of free radical initiators. Preferably used initiators are peroxy esters, such as tert-butyl per-2-ethylhexanoate. In addition to the homopolymers, copolymers of maleic anhydride are suitable, for example copolymers of acrylic acid and maleic anhydride or copolymers of maleic anhydride and $C_2$–$C_{30}$-olefin.

For example, copolymers of maleic anhydride and isobutene or copolymers of maleic anhydride and diisobutene are preferred. The copolymers containing anhydride groups can, if required, be modified by reaction with $C_1$–$C_{20}$-alcohols or ammonia or amines and can be used in this form as crosslinking agents.

The molar mass $M_w$ of the homo- and copolymers is, for example, up to 10,000, preferably from 500 to 5000. Polymers of the abovementioned type are described, for example, in EP-A-0 276 464, U.S. Pat. No. 3,810,834, GB-A-1 411 063 and U.S. Pat. No. 4,818,795. The at least dibasic saturated carboxylic acids and polycarboxylic acids can be used as crosslinking agents also in the form of the alkali metal or ammonium salts. The sodium salts are preferably used. The polycarboxylic acids may be partially neutralized, for example to an extent of from 10 to 50 mol %, or completely neutralized.

Preferably used compounds of the group (2) are dimethyl tartrate, diethyl tartrate, dimethyl adipate, diethyl adipate, dimethyl maleate, diethyl maleate, maleic anhydride, maleic acid, acrylic acid, methyl acrylate, ethyl acrylate, acrylamide and methacrylamide.

Halogen-free crosslinking agents of the group (3) are, for example, reaction products of polyetherdiamines, alkylenediamines, polyalkylenepolyamines, alkylene glycols, polyalkylene glycols or mixtures thereof with
    monoethylenically unsaturated carboxylic acids,
    esters of monoethylenically unsaturated carboxylic acids,
    amides of monoethylenically unsaturated carboxylic acids
    or
    anhydrides of monoethylenically unsaturated carboxylic acids.

The polyetherdiamines are prepared, for example, by reacting polyalkylene glycols with ammonia. The polyalkylene glycols may contain from 2 to 50, preferably from 2 to 40, alkylene oxide units. These may be, for example, polyethylene glycols, polypropylene glycols, polybutylene glycols or block copolymers of ethylene glycol and propylene glycol, block copolymers of ethylene glycol and butylene glycol or block copolymers of ethylene glycol, propylene glycol and butylene glycol. In addition to the block copolymers, random copolymers of ethylene oxide and propylene oxide and, if required, butylene oxide are suitable for the preparation of polyetherdiamines. Polyetherdiamines are also derived from polytetrahydrofurans which have from 2 to 75 tetrahydrofuran units. The polytetrahydrofuran are likewise converted into the corresponding α,ωpolyetherdiamines by reaction with ammonia. Polyethylene glycols or block copolymers of ethylene glycol and propylene glycol are preferably used for the preparation of the polyetherdiamines.

Examples of suitable alkylenediamines are ethylenediamine, propylenediamine, 1,4-diaminobutane and 1,6-diaminohexane. Examples of suitable polyalkylenepolyamines are diethylenetriamine, triethylenetetramine, dipropylenetriamine, tripropylenetetramine, dihexamethylenetriamine, aminopropylethylenediamine, bisaminopropylethylenediamine and polyethyleneimines having molar masses of up to 5000. The amines described above are reacted with monoethylenically unsaturated carboxylic acids, esters, amides or anhydrides of monoethylenically unsaturated carboxylic acids so that the resulting products have at least 2 ethylenically unsaturated double bonds or carboxamido, carboxyl or ester groups as functional groups. Thus, compounds which may be characterized, for example, with the aid of the formula II:

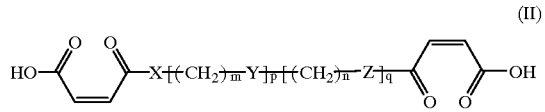

(II)

where

X, Y, Z are each O or NH and Y may additionally be $CH_2$ m, n are each 0–4 and p, q are each 0–45000, are obtained, for example, in the reaction of the suitable amines or glycols with maleic anhydride.

The compounds of the formula (II) are obtainable, for example, by reacting alkylene glycols, polyethylene glycols, polyethyleneimines, polypropyleneimines, polytetrahydrofurans, $\alpha,\omega$-diols or $\alpha,\omega$-diamines with maleic anhydride or the abovementioned other monoethylenically unsaturated carboxylic acids or carboxylic acid derivatives. The polyethylene glycols which are suitable for the preparation of the crosslinking agents II preferably have molar masses of from 62 to 10,000, the molar masses of the polyethyleneimines are preferably from 129 to 50,000 and those of the polypropyleneimines are from 171 to 50,000. Examples of suitable alkylene glycols are ethylene glycol, 1,2-propylene glycol, 1,4-butanediol and 1,6-hexanediol.

Preferably used $\alpha,\omega$-diamines are ethylenediamine and $\alpha,\omega$-diamines derived from polyethylene glycols or from polytetrahydrofurano having molar masses Mw of from about 400 to 5000 in each case.

Particularly preferred crosslinking agents of the formula II are reaction products of maleic anhydride with $\alpha,\omega$-polyetherdiamines having a molar mass of from 400 to 5000, the reaction products of polyethyleneimines having a molar mass of 129 to 50,000 with maleic anhydride and the reaction products of ethylenediamine or triethylenetetramine with maleic anhydride in a molar ratio of 1: at least 2. In the reaction of polyalkylene glycols or diols with monoethylenically unsaturated carboxylic acids or their esters, amides or anhydrides, crosslinking agents in which the monoethylenically unsaturated carboxylic acids or their derivatives are linked to the polyetherdiamines, alkylenediamines or polyalkylenepolyamines via an amido group and to the alkylene glycols or polyalkylene glycols via an ester group are formed, with retention of the double bond of the monoethylenically unsaturated carboxylic acids or their derivatives. These reaction products contain at least two ethylenically unsaturated double bonds. This type of crosslinking agent undergoes a Michael addition reaction with the amino groups of the compounds to be crosslinked, the reaction taking place at the terminal double bonds of these crosslinking agents and possibly also with formation of amido groups.

Polyetherdiamines, alkylenediamines and polyalkylenepolyamines can undergo a Michael addition with maleic anhydride or the ethylenically unsaturated carboxylic acids or derivatives thereof, also with addition of the double bond. Crosslinking agents of the formula III

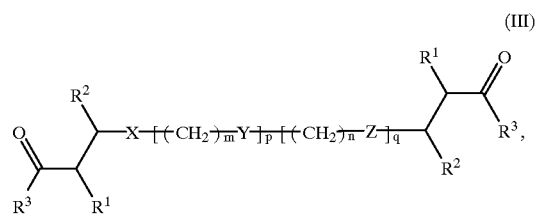

(III)

where

X, Y, Z are each O or NH and Y may additionally be $CH_2$, $R^1$ is H or $CH_3$, $R^2$ is H, COOMe, COOR or $CONH_2$, $R^3$ is OR, $NH_2$, OH or OMe, R is $C_1$–$C_{22}$-alkyl, Me is H, Na, K, Mg or Ca m, n are each 0–4 and p, q are each 0–45,000, are obtained here.

The amino-containing compounds are crosslinked by means of the crosslinking agents of the formula (III) by their terminal carboxyl or ester groups with formation of an amido function. This class of crosslinking systems includes the reaction products of monoethylenically unsaturated carboxylic esters with alkylenediamines and polyalkylenepolyamines, for example, the adducts of ethylenediamine, diethylenetriamine, triethylenetetramine and tetraethylenepentamine and of polyethyleneimines having molar masses of, for example, from 129 to 50,000 with acrylates or methacrylates are suitable, at least 2 mol of the acrylate or methacrylate being used per mol of the amine component. Preferably used esters are monoethylenically unsaturated carboxylic acids of the $C_1$–$C_6$-alkyl esters or acrylic acid or methacrylic acid. Methyl acrylate and ethyl acrylate are preferred for the preparation of the crosslinking agents. The crosslinking agents which are prepared by a Michael addition of the polyalkylenepolyamines and ethylenically unsaturated carboxylic acids, esters, amides or anhydrides may have more than two functional groups. The number of these groups depends on the molar ratio in which the reactants are used in the Michael addition reaction. For example, from 2 to 10, preferably from 2 to 8, mol of ethylenically unsaturated carboxylic acids or their derivatives may be subjected to a Michael addition reaction with one mol of a polyalkylenepolyamine containing 10 nitrogen atoms. From at least 2 to not more than 4 mol of the ethylenically unsaturated carboxylic acids or their derivatives may be subjected to a Michael addition reaction with, in each case, 1 mol of polyalkylenediamines and alkylenediamines.

In the reaction of diethylenetriamine and a compound of the formula

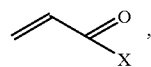

where X is OH, $NH_2$ or $OR^1$ and $R^1$ is $C_1$–$C_{22}$-alkyl, for example a crosslinking agent of the structure

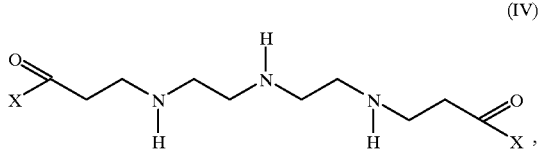

where
X is $NH_2$, OH or $OR^1$ and
$R^1$ is $C_1$–$C_{22}$-alkyl,
is formed by a Michael addition reaction.

The secondary NH groups in the compounds of the formula IV may undergo a Michael addition reaction with acrylic acid, acrylamide or acrylates.

The compounds of the formula II which contain at least 2 carboxyl groups and are obtainable by reacting polyetherdiamines, ethylenediamine or polyalkylenepolyamines with maleic anhydride, or Michael adducts containing at least 2 ester groups and obtained from polyetherdiamines, polyalkylenepolyamines or ethylenediamine and esters of acrylic acid or methacrylic acid with, in each case, monohydric alcohols of 1 to 4 carbon atoms are preferably used as crosslinking agents of the group (3).

Suitable halogen-free crosslinking agents of the group (4) are reaction products which are prepared by reacting dicarboxylic esters which are completely esterified with monohydric alcohols of 1 to 5 carbon atoms with ethyleneimine. Examples of suitable dicarboxylic esters are dimethyl oxalate, diethyl oxalate, dimethyl succinate, diethyl succinate, dimethyl adipate, diethyl adipate and dimethyl glutarate. Thus, bis[b-(1-aziridino)ethyl]oxalamide is obtained, for example, in the reaction of diethyl oxalate with ethyleneimine. The dicarboxylic esters are reacted with ethyleneimine, for example in a molar ratio of 1 to at least 4. Reactive groups of these crosslinking agents are the terminal aziridino groups. These crosslinking agents can be characterized, for example, with the aid of the formula V:

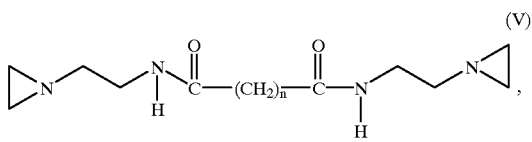

where n is from 0 to 22.

The crosslinking agents described above may be used either alone or as a mixture in the reaction with water-soluble, amino-containing polymers, diamines or polyalkylenepolyamines. The crosslinking reaction is continued in all cases only so far that the resulting products are still water-soluble, for example at least 10 g of the crosslinked polymers should dissolve in 1 l of water at 20° C. The crosslinking reaction is carried out in a known manner by heating the reaction components at from 50 to 220° C., preferably from 60 to 100° C. If the crosslinking reaction is carried out at above 100° C. in an aqueous medium, pressure-tight apparatuses, for example an autoclave equipped with a stirrer, are required for this purpose.

Other suitable water-soluble, amino-containing polymers are reaction products which are obtainable by reacting Michael adducts of polyalkylenepolyamines, polyamidoamines, polyamidoamines with ethyleneimine grafted and mixtures of the stated compounds and monoethylenically unsaturated carboxylic acids, salts, esters, amides or nitrites with at least bifunctional crosslinking agents. Such reaction products are disclosed, for example, in WO-A-94/184743. In addition to the halogen-containing crosslinking agents, the classes of halogen-free crosslinking agents described above are particularly suitable for their preparation.

A further class of polymers containing amino groups, preferably ethyleneimine units, is disclosed in WO-A-94/12560. These are water-soluble, crosslinked, partially amidated polyethyleneimines which are obtainable by
  reacting polyethyleneimines with monobasic carboxylic acids or their esters, anhydrides, acyl chlorides or amides with amide formation and
  reacting the amidated polyethyleneimines with crosslinking agents containing at least two functional groups.

The monobasic carboxylic acids have, for example, 1 to 28, preferably 8 to 18, carbon atoms and may, if required, contain one or more ethylenic double bonds, for example oleic acid or linolenic acid.

The molar masses of the suitable polyethyleneimines may be up to 2 million and are preferably from 1000 to 50,000. The polyethyleneimines are partially amidated with monobasic carboxylic acids, so that, for example, from 0.1 to 90, preferably from 1 to 50, % of the amidatable nitrogen atoms are present as amido groups in the polyethyleneimines. Suitable crosslinking agents containing at least two functional double bonds are stated above. Halogen-free crosslinking agents are preferably used.

In the reaction of amino-containing compounds with crosslinking agents, for example, from 0.001 to 10, preferably 0.01 to 3, parts by weight of at least one crosslinking agent are used per part by weight of an amino-containing compound.

Other amino-containing adducts which are used in the ultrafiltration are polyethyleneimines and quaternized polyethyleneimines. For example, both homopolymers of ethyleneimine and polymers which contain, for example, ethyleneimine grafted on are suitable for this purpose. The homopolymers are prepared, for example, by polymerizing ethyleneimine in aqueous solution in the presence of acids, Lewis acids or alkylating agents, such as methyl chloride, ethyl chloride, propyl chloride, ethylene chloride, chloroform or tetrachloroethylene. The polyethyleneimines thus obtainable have a broad molar mass distribution and molar masses of, for example, from 129 to $2 \cdot 10^6$, preferably from 430 to $1 \cdot 10^6$.

The polyethyleneimines and the quaternized polyethyleneimines may, if required, have been reacted with a crosslinking agent containing at least two functional groups. The quaternization of the polyethyleneimines may be carried out, for example, with alkyl halides, such as methyl chloride, ethyl chloride, hexyl chloride, benzyl chloride [sic] or lauryl chloride or with, for example, dimethyl sulfate. Further suitable amino-containing polymers whose quality can be improved by ultrafiltration are polyethyleneimines modified by a Strecker reaction, for example the reaction products of polyethyleneimines with formaldehyde and sodium cyanide with hydrolysis of the resulting nitriles to the corresponding carboxylic acids. These products may, if required, have been reacted with a crosslinking agent containing at least two functional groups.

Phosphonomethylated polyethyleneimines and alkoxylated polyethyleneimines which are obtainable, for example, by reacting polyethyleneimine with ethylene oxide and/or propylene oxide are also suitable. The phosphonomethylated and the alkoxylated polyethyleneimines may, if required, have been reacted with a crosslinking agent containing at least two functional groups. The alkoxylated polyethyleneimines contain from 1 to 100, preferably from 2 to 20, alkylene oxide units per NH group. The molar mass of the polyethyleneimines may be up to 2 million. Polyethyleneimines having molar masses of from 1000 to 50,000 are preferably used for the alkoxylation. Further suitable water-soluble amino-containing polymers are reaction products of polyethyleneimines with diketenes, for example of polyethyleneimines having a molar mass of from 1000 to 50,000 with distearyl diketene. Such products, too, may, if required, have been reacted with a crosslinking agent containing at least two functional groups. Further suitable water-condensates are crosslinked polyethyleneimines which are carboxymethylated by a Strecker reaction and are obtainable by reacting carboxymethylated polyethyleneimines with at least one of the above-mentioned crosslinking agents.

The water-soluble amino-containing polymers described above and having a broad molar mass distribution are subjected, according to the invention, to the ultrafiltration. The low molecular weight fractions of condensates or adducts separated off as permeate may be recycled, in the preparation process, to the water-soluble polymers used as starting materials in the ultrafiltration, ie. they are used for the synthesis of water-soluble, amino-containing polymers having a broad molecular weight distribution, which are then subjected again to the ultrafiltration through membranes, from 5 to 95% by weight, based on the polymers used, of low molecular weight polymers being separated off as permeate. The low molecular weight fractions can thus be separated off from the water-soluble amino-containing polymers having a broad molar mass distribution and, after an increase in the molar mass in the process, can be recycled to the ultrafiltration. If the concentration of the isolated low molecular weight polymer fractions in the permeate is too low, the permeate is concentrated by distilling off water; for example, a concentration of from 5 to 50, preferably from 10 to 30, % by weight of polymer is established. The low molecular weight polymer fractions contained in the permeate separated off can, for example, be grafted with ethyleneimine. The reaction is carried out in the aqueous medium, for example at from 50 to 200° C. with the action of acids, such as sulfuric acid or phosphoric acid, or of Lewis acids.

The low molecular weight fractions of amino-containing polymers which are separated off with the permeate in the ultrafiltration can also be reacted with crosslinking agents having at least two functional groups to give higher molecular weight polymers having a broad molar mass distribution, which are then again subjected to the ultrafiltration. Suitable crosslinking agents have been stated above.

The low molecular weight polymer fractions separated off in the ultrafiltration can also be worked up to obtain products having a broad molar mass distribution by first reacting them with ethyleneimine and reacting the reaction products obtainable thereby with crosslinking agents having at least two functional groups. These polymers obtainable in this manner and having a broad molar mass distribution are recycled to the ultrafiltration in order to obtain therefrom the high molecular weight fractions having a narrower molar mass distribution and a viscosity of at least 120 mPa·s (measured in 10% strength by weight aqueous solution at 20° C. and pH 10). The higher molecular weight or high molecular weight fractions of polymers containing ethyleneimine units, which fractions are obtained as retentate, can, if required, be isolated from the aqueous solutions by, for example, evaporating off the water. The predominant part of the polymers containing ethyleneimine units and having a narrower molar mass distribution is, however, used in the form of a solution. For example, in the case of the polyamidoamines grafted with ethyleneimine and crosslinked, the concentration of the aqueous solutions is from 5 to 25, preferably from 7 to 20, % by weight.

Particularly preferably used water-soluble condensates and/or adducts containing amino groups are those reaction products which are obtainable by grafting polyamidoamines with ethyleneimine and then reacting the product with crosslinking agents containing at least two functional groups. Preferred crosslinking agents for this purpose are halogen-free bifunctional compounds which are selected from the group consisting of (1) ethylene carbonate, propylene carbonate and/or urea,
(2) monoethylenically unsaturated carboxylic acids and esters, amides and anhydrides thereof, at least dibasic saturated carboxylic acids or polycarboxylic acids and the esters, amides and anhydrides derived from each of them,
(3) reaction products of polyetherdiamines, alkylenediamines, polyalkylenepolyamines, alkylene glycols, polyalkylene glycols or mixtures thereof with monoethylenically unsaturated carboxylic acids, esters, amides or anhydrides of monoethylenically unsaturated carboxylic acids, the reaction products having at least two ethylenically unsaturated double bonds, and carboxamido, carboxyl or ester groups as functional groups,
(4) reaction products of dicarboxylic esters with ethyleneimine, which reaction products contain at least two aziridino groups, and mixtures of the stated crosslinking agents, and block polymers of ethylene oxide and propylene oxide or polyalkylene glycols blocked at both ends with epichlorohydrin terminal groups. Crosslinked polyamidoamines grafted with ethyleneimine and based on adipic acid and diethylenetriamine and/or triethylenetetramine are particularly preferably used. Such condensates are disclosed, for example, in U.S. Pat. No. 4,144,123 stated in connection with the prior art. Particularly preferred crosslinked polyamidoamines grafted with ethyleneimine include those reaction products which are obtainable in the presence of halogen-free crosslinking agents based on Michael adducts of polyetherdiamines having molar masses of from 400 to 5000 or of polyamines having molar masses of from 129 to 50,000 with acrylates or of reaction products of maleic anhydride with polyetherdiamines (cf. formula II).

Water-soluble, amino-containing condensates or adducts having a molar mass distribution $M_w/M_n$ of from 2 to 350 and a viscosity of at least 120 mPa·s in 10% strength aqueous solution at 20° C. and pH 10 are obtained as retentate in the ultrafiltration. These amino-containing polymers having a narrower molecular weight distribution are used as retention aids, drainage aids, flocculants and fixing compositions in papermaking. For this purpose, they are added to the paper stock in the usual amounts of, for example, from 0.01 to 1% by weight. Compared with the same amount of amino-containing polymers of the same composition which have a broad molecular weight distribution, a surprisingly increased retention and drainage effect is obtained with that fraction of water-soluble amino-containing condensates and/or adducts which remains in the retentate.

The polymer fractions obtained as retentate are also very useful in combination with anionic, neutral or cationic high molecular weight polyacrylamides, as retention aids, drainage aids or fixing compositions. Similar systems are disclosed in the literature, cf. EP-A-0 223 223, EP-A-0 235 893 and EP-A-0 335 575.

Combinations of the polymer fractions obtained as retentate with colloidal silica or bentonites, alone or additionally with anionic, neutral or cationic high molecular weight polyacrylamides as a third component, are very particularly useful as retention aids, draining aids or fixing compositions in papermaking. Processes for the production of paper with cationic assistants which have not been subjected to any particular aftertreatment, for example ultrafiltration, are disclosed, for example, in EP-A-0 223 223, EP-A-0 235 893 and EP-A-0 335 575. If the retentates of amino-containing condensates or adducts, obtainable by the novel ultrafiltration method, are used in the process disclosed, for example, in the abovementioned literature publications, a significant improvement in the drainage rate and retention is achieved in papermaking.

The polymer fractions obtained as retentate in the ultrafiltration are moreover used as flocculants for sewage sludges, as adhesion promoters in the production of laminated films, as additives in hair and skincare compositions and as compositions for immobilizing anionic active ingredients for example in the production of medicaments.

The retentates obtainable in the ultrafiltration and containing polyethyleneimines which have a molar mass of, for example, from $10^5$ to $2 \cdot 10^6$ are preferably used as adhesion promoters for the production of laminated films. Such retentates give stronger bonds having higher aging resistance. Since the low molecular weight components are separated off from the polyethyleneimines subjected to ultrafiltration, the retentates are particularly suitable as primers for the production of food packaging and as additives in hair and skincare compositions.

In the examples which follow, percentages are by weight unless stated otherwise.

Unless indicated otherwise in the examples, the viscosities were measured in a Brookfield viscometer at 20° C., a concentration of 10% by weight and a pH of 10.

In the examples in which an ultrafiltration is described, hollow fiber cartridges from A/G-Technology Corp., Needham, Mass., USA, were used in each case. The cut-offs of the membranes of the hollow fiber cartridges are stated in the examples. The ultrafiltration was terminated in all cases as soon as the conductivity of the permeate fell below 200 mS/cm.

EXAMPLES

Polymers 1a) and 1b)

Polymer 1a)

Using the method stated in DE-B-24 34 816, Example 3, a polyamide or amine is prepared by condensation of adipic acid with diethylenetriamine and was subsequently grafted in aqueous solution with ethyleneimine in an amount such that the polyamidoamine contains 6.7 ethyleneimine units grafted on per basic nitrogen group. A 10% strength aqueous solution of the polymer has a viscosity of 22 mPa·s.

Polymer 1b)

Polymer 1a (polyamidoamine grafted with ethyleneimine) is crosslinked by reaction with a bisglycidyl ether of a polyethylene glycol having an average molar mass of 2000, according to Example 3 of DE-B-24 34 816. A polymer containing ethyleneimine units and having a broad molar mass distribution ($M_w/M_n$ of 400) and a viscosity of 120 mPa·s (determined in 10% aqueous solution at 20° C. and pH 10) is obtained. The concentration of the aqueous solution is 12.5% and pH is 10.

Polymer 2

Copolymer of acrylamide and dimethylaminoethyl acrylate, which is quaternized with methyl chloride, contains 84 mol % of acrylamide and has a molar mass of about 10 million.

Example 1

4.8 kg of the 12.5% strength aqueous solution of polymer 1b described above was subjected to the ultrafiltration through a membrane having a cut-off for polymers with molar masses of 100,000. The membranes were in the form of a hollow fiber cartridge. The volume on the retentate side was maintained by adding 10 kg of water. The ultrafiltration was terminated after the conductivity of the permeate was below 200 mS/cm. After completion of the ultrafiltration, 40% of water-soluble polymer 1b containing ethyleneimine units and having a molar mass distribution $M_w/M_n$ of 15 were present on the retentate side. The viscosity of the polymer having a narrower molecular weight distribution was 520 mPa·s (measured in 10% strength aqueous solution at pH 10 and 20° C.). 60%, based on polymer 1b, were separated off as permeate. The permeate was concentrated to 45% with the aid of a falling-film evaporator. The viscosity of the low molecular weight fractions separated off was 24 mPa·s (determined in 10% strength aqueous solution at 20° C. and pH 10).

Example 2

Example 1 was repeated, except that 2 kg of water were added to maintain the volume on the retentate side. After completion of the ultrafiltration, 60%, based on polymer 1b, were present on the retentate side. This polymer had a molar mass distribution $M_w/M_n$ of 300 and a viscosity of 150 mPa·s (measured in 10% strength aqueous solution at 20° C.). The polymer concentration of the permeate was brought to 45% by distilling off water by means of a falling-film evaporator. The low molecular weight polymer fractions of the permeate had a viscosity of 25 mPa·s.

Example 3

In a flask equipped with a stirrer and a reflux condenser, 1.7 g of 96% strength sulfuric acid were added to 100 g of the low molecular weight polymer separated off in Example 1, in the form of the 45% strength aqueous solution, and the mixture was heated to 85° C. As soon as this temperature had been reached, 50 g of ethyleneimine in the form of a 60% strength aqueous solution were added. 66 g of water were added in the course of the reaction, which lasted for 6 hours.

Example 4

In a flask provided with a stirrer and reflux condenser, 100 g of the low molecular weight fractions separated off according to Example 1 were initially taken as a 45% strength aqueous solution, 1.7 g of 96% strength sulfuric acid were added and the mixture was heated to 90° C. As soon as this temperature had been reached, 100 g of ethyleneimine in the form of a 60% strength aqueous solution were added and a further 107 g of water were added in the course of the reaction.

Example 5

50 g of low molecular weight polymer which was obtained as permeate in Example 1 were initially taken as a 25% strength aqueous solution in a flask equipped with a stirrer and reflux condenser. At 70° C., 13.5 g of a 20% strength aqueous solution of the bisglycidyl ether of a polyethylene glycol of molar mass 2000 were added. The pH of the reaction mixture was then brought to 7.8. The reaction solution had a solids content of 26.6% and a viscosity of 625 mPa·s.

Example 6

50 g of the reaction product from Example 3 were initially taken as a 25% strength aqueous solution in a reactor, heated to 70° C. and crosslinked by adding 12 g of a bisglycidyl ether of polyethylene glycol having a molar mass of 2000 in the form of a 20% strength aqueous solution. The pH of the reaction product was brought to 7.8. The aqueous solution had a solids content of 26% and a viscosity of 670 mPa·s.

Example 7

50 g of the reaction product described in Example 4 were initially taken in the form of a 25% strength aqueous solution in a reactor and crosslinked, at 70° C., with 10 g of the bisglycidyl ether of a polyethylene glycol of molar mass 2000 in the form of a 20% strength aqueous solution. The pH was brought to 7.8 after the reaction. An aqueous solution having a solids content of 27.1% and a viscosity of 610 mPa·s (determined at 20° C.) was obtained.

The products described above were tested as drainage aids, retention aids and fixing compositions in papermaking. The Schopper-Riegler drainage time was determined as a measure of the drainage power. The optical transmittance of the outflowing white water was used as a measure of the retention of fibers, crill and fillers. The measurements were carried out with the aid of a photometer from Lange at 588 nm.

The extinction (Lange photometer, 340 nm) in water treated with fixing composition was determined as a measure of the fixing power for crill and fillers (purification of contaminated closed water circulations). Polymer 1b was used as a comparison with the prior art.

The measured results stated below are mean values of 5 measurements. Retention aids and drainage aids were added to the paper stock in amounts of from 0.01 to 0.08, and fixing compositions in amounts of from 0.01 to 2% by weight, based in is each case on the solids.

Example 8

A pulp having a consistency of 5 g/l and a freeness of 505SR (Schopper-Riegler) was produced from 100 parts of unprinted newsprint having a filler content of 10% and containing 40 parts of natural chalk (type DX 1 from Omya). The pH of the pulp was 7.7. The paper stock was divided into several samples, to which the amounts of polymers stated in Table 1 were then added. The drainage times for 600 ml of filtrate in each case were determined for each sample in the Schopper-Riegler tester.

In contrast to the abovementioned method, in Comparative Example 1 the drainage rate was determined for the abovementioned paper stock in the absence of a polymer. The results are shown in each case in Table 1.

TABLE 1

| Example 8 | Polymer used | Amount of polymer, based on dry paper stock [%] | Drainage time [sec] |
| --- | --- | --- | --- |
| a) | Retentate of Example 1 | 0.01 | 261 |
| b) | Retentate of Example 1 | 0.02 | 154 |
| c) | Retentate of Example 1 | 0.04 | 65 |
| d) | Retentate of Example 1 | 0.08 | 28 |
| Comparative Example | | | |
| 1 | — | — | 402 |
| 2a) | Polymer 1b | 0.02 | 263 |
| 2b) | " | 0.04 | 168 |
| 2c) | " | 0.08 | 89 |
| 3a) | Polymer 2 | 0.01 | 315 |
| 3b) | " | 0.02 | 218 |
| 3c) | " | 0.04 | 82 |

Example 9

The amounts of polymer stated in Table 2 were added to the paper stock described in Example 8, with the exception of Comparative Example 4, and said paper stock was processed in each case on an experimental paper machine having a fourdrinier wire and a connected Akumat (top wire) at a machine speed of 50 m/min and a web width of 74 cm to give paper having a basis weight of 80 g/m$^2$. The filler content of the paper was automatically determined in each case with the aid of an automatic measuring unit. The filler content of the paper is shown in each case in Table 2. It is a measure of the filler retention.

TABLE 2

| Example 9 | Polymer used | Amount of polymer, based on dry paper stock [%] | Filler content of the paper [%] |
| --- | --- | --- | --- |
| a) | Retentate of Example 1 | 0,01 | 29.4 |
| b) | Retentate of Example 1 | 0.02 | 34.3 |
| c) | Retentate of Example 1 | 0.04 | 35.5 |
| d) | Retentate of Example 1 | 0.08 | 35.7 |
| Comparative Example | | | |
| 4 | — | — | 18 |
| 5a) | Polymer 1b | 0.02 | 30.2 |
| 5b) | " | 0.04 | 34.2 |
| 5c) | " | 0.08 | 35.6 |

TABLE 2-continued

| Example 9 | Polymer used | Amound of polymer, based on dry paper stock [%] | Filler content of the paper [%] |
|---|---|---|---|
| 6a) | Polymer 2 | 0.01 | 28.7 |
| 6b) | " | 0.02 | 32.0 |
| 6c) | " | 0.04 | 35.7 |

Example 10

A pulp having a consistency of 5 g/l and a freeness of 505 SR was produced from 100 parts of printed newsprint. The pH of the pulp was 7.7. The amounts of polymers stated in each case in Table 3 were added to samples of this paper stock, with the exception of Comparative Example 7, and the drainage times for 600 ml of filtrate were measured in each case in a Schopper-Riegler tester. The results obtained are shown in Table 3.

TABLE 3

| Example 10 | Polymer used | Amount of polymer, based on dry paper stock [%] | Drainage time [sec] |
|---|---|---|---|
| a) | Retentate of Example 1 | 0.01 | 265 |
| b) | Retentate of Example 1 | 0.02 | 175 |
| c) | Retentate of Example 1 | 0.04 | 76 |
| d) | Retentate of Example 1 | 0.08 | 42 |
| Comparative Example | | | |
| 7 | — | — | 404 |
| 8a) | Polymer 1b | 0.02 | 283 |
| 8b) | " | 0.04 | 173 |
| 8c) | " | 0.08 | 95 |
| 9a) | Polymer 2 | 0.01 | 243 |
| 9b) | " | 0.02 | 135 |

Example 11

The amounts of polymers stated in Table 4 were added in each case to the paper stock described in Example 10, and said paper stock was drained on an experimental paper machine having a fourdrinier wire and a connected Akumat and a web width of 74 cm at a machine speed of 55 m/min to give paper having a basis weight of 70 g/m². The filler content of the paper, which is a measure of the filler retention, was determined with the aid of an automatic measuring unit. The results obtained are shown in Table 4. In Comparative Example 10, the paper stock described in Example 10 were drained without further addition.

TABLE 4

| Example 11 | Polymer used | Amound of polymer, based on dry paper stock [%] | Filler content of the paper [%] |
|---|---|---|---|
| a) | Retentate of Example 1 | 0.01 | 7.1 |
| b) | Retentate of Example 1 | 0.02 | 8.3 |
| c) | Retentate of Example 1 | 0.04 | 10.7 |
| d) | Retentate of Example 1 | 0.08 | 10.5 |
| Comparative Example | | | |
| 10 | — | — | 4.9 |
| 11a) | Polymer 1b | 0.02 | 8.0 |
| 11b) | " | 0.04 | 8.9 |
| 11c) | " | 0.08 | 9.5 |
| 12a) | Polymer 2 | 0.01 | 7.5 |
| 12b) | " | 0.02 | 8.2 |
| 12c) | " | 0.04 | 9.2 |

Example 12

A pulp having a consistency of 5 g/l and a freeness of 27° SR was produced from 50 parts of bleached pine sulfate pulp, 50 parts of bleached beech sulfite pulp and 30 parts of a natural chalk (type DX 1 from Omya). The pH of the pulp was 7.2. The amounts of polymer stated in Table 5 were added to samples of this paper stock, with the exception of Comparative Example 13, and the drainage times for 600 ml of filtrate were determined in each case in a Schoppler-Riegler tester. The drainage times are shown in Table 5.

TABLE 5

| Example 12 | Polymer used | Amount of polymer, based on dry paper stock [%] | Drainage time [sec] |
|---|---|---|---|
| a) | Retentate of Example 1 | 0.02 | 60 |
| b) | Retentate of Example 1 | 0.04 | 35 |
| Comparative Example | | | |
| 13 | — | — | 114 |
| 14a) | Polymer 1b | 0.02 | 96 |
| 14b) | " | 0.04 | 65 |
| 15 | Polymer 2 | 0.02 | 90 |

Example 13

The amounts of polymer stated in Example 6 were added from [sic] the paper stock described in Example 12, with the exception of Comparative Example 16. Paper having a basis weight of 70 g/m² was produced on an experimental paper machine having a fourdrinier wire and a connected Akumat (top wire) and a web width of 74 cm at different machine speeds. The filler content of the papers was determined with the aid of an automatic measuring unit. The experimental conditions and results are shown in Table 6.

TABLE 6

| Example 13 | Polymer used | Amount of polymer, based on dry paper stock [%] | Machine speed [m/min] | Filler content of the paper [%] |
|---|---|---|---|---|
| a) | Retentate of Example 1 | 0.02 | 50 | 27.7 |
| b) | Retentate of Example 1 | 0.04 | 52 | 29.1 |
| Comparative Example | | | | |
| 16 | — | — | 40 | 11.2 |
| 17a) | Polymer 1b | 0,02 | 46 | 25.4 |
| 17b) | " | 0.04 | 48 | 27.5 |
| 18a) | Polymer 2 | 0.01 | 48 | 18.2 |
| 18b) | " | 0.02 | 50 | 24.8 |

Example 14

A pulp having a consistency of 5 g/l and a freeness of 50° SR was produced from 100 parts of unprinted newsprint having a filler content of about 10% and containing 10 parts of china clay (type X 1 from ECC). The pH was 7.6. The amounts of polymer stated in Table 7 were added in each case to this paper stock, with the exception of Comparative Example 19, and the drainage times of the paper stocks thus obtained were determined in a Schopper-Riegler tester and the optical transmittance of the white water was measured. The results are shown in Table 7.

TABLE 7

| Example 14 | Polymer used | Amount of polymer, based on dry paper stock [%] | Drainage time [sec] | Optical transmittance [%] |
|---|---|---|---|---|
| a) | Retentate of Example 1 | 0.02 | 41 | 64 |
| b) | Retentate of Example 1 | 0.04 | 27 | 79 |
| c) | Retentate of Example 1 | 0.06 | 21 | 80 |
| b) | Retentate of Example 1 | 0.08 | 19 | 84 |
| Comparative Example | | | | |
| 19 | — | — | 92 | 23 |
| 20a) | Polymer 1b | 0.02 | 58 | 52 |
| 20b) | " | 0.04 | 43 | 65 |
| 20c) | " | 0.06 | 34 | 71 |
| 20d) | " | 0.08 | 30 | 74 |

Examples 15 to 17

A pulp having a consistency of 2.2 g/l and a freeness of 50° SR was produced from 100 parts of unprinted newsprint having a filler content of 10% and containing 10 parts of china clay from ECC, type X 1. The pH of the pulp was 7. The polymer stated in each case in Table 8, in the amount designated there, was added to samples of this paper stock, with the exception of Comparative Example 21. After thorough mixing, the samples were each drained in a Schopper-Riegler tester and the drainage time for 600 ml of filtrate was determined. Table 8 also shows the optical transmittance of the filtrate.

TABLE 8

| Example | Polymer used | Amount of polymer, based on dry paper stock [%] | Drainage time [sec] | Optical transmittance [%] |
|---|---|---|---|---|
| 15a) | Polymer prepared acccording to Example 5 | 0.02 | 55 | 48 |
| 15b) | Polymer prepared acccording to Example 5 | 0.04 | 43 | 62 |
| 15c) | Polymer prepared acccording to Example 5 | 0.06 | 36 | 69 |
| 15d) | Polymer prepared acccording to Example 5 | 0.08 | 29 | 75 |
| 16a) | Polymer prepared according to Example 6 | 0.02 | 54 | 51 |
| 16b) | Polymer prepared according to Example 6 | 0.04 | 38 | 66 |
| 16c) | Polymer prepared according to Example 6 | 0.06 | 30 | 74 |
| 16d) | Polymer prepared according to Example 6 | 0.08 | 26 | 76 |
| 17a) | Polymer prepared acccording to Example 7 | 0.02 | 54 | 48 |
| 17b) | Polymer prepared acccording to Example 7 | 0.04 | 38 | 66 |
| 17c) | Polymer prepared acccording to Example 7 | 0.06 | 29 | 73 |
| 17d) | Polymer prepared acccording to Example 7 | 0.08 | 25 | 77 |

TABLE 8-continued

| Example | Polymer used | Amount of polymer, based on dry paper stock [%] | Drainage time [sec] | Optical transmittance [%] |
|---|---|---|---|---|
| Comparative Example | | | | |
| 21a) | Polymer 1b | 0.02 | 53 | 52 |
| 21b) | " | 0.04 | 38 | 65 |
| 21c) | " | 0.06 | 31 | 76 |
| 21d) | " | 0.08 | 26 | 78 |
| 22 | — | — | 84 | 26 |

Examples 18 to 20

A pulp having a consistency of 2.2 g/l and a freeness of 50° SR was produced from 100 parts of unprinted newsprint having a filler content of about 10% and containing 10 parts of china clay from ECC, type X 1, and 0.5%, based on dry stock, of alum. The pH of the pulp was 6.0. The amounts of polymers stated in each case in Table 9 were added to samples of this paper stock, with the exception of Comparative Example 23, and the drainage time for 600 ml of filtrate was determined in a Schopper-Riegler tester. Table 9 also shows the optical transmittance of the filtrate.

TABLE 9

| Example | Polymer used | Amount of polymer, based on dry paper stock [%] | Drainage time [sec] | Optical transmittance [%] |
|---|---|---|---|---|
| 18a) | Polymer prepared according to Example 5 | 0.02 | 47 | 56 |
| 18b) | Polymer prepared according to Example 5 | 0.04 | 37 | 63 |
| 18c) | Polymer prepared according to Example 5 | 0.06 | 33 | 68 |
| 18d) | Polymer prepared according to Example 5 | 0.08 | 30 | 71 |
| 19a) | Polymer prepared according to Example 6 | 0.02 | 47 | 58 |
| 19b) | Polymer prepared according to Example 6 | 0.04 | 34 | 69 |
| 19c) | Polymer prepared according to Example 6 | 0.06 | 29 | 75 |
| 19d) | Polymer prepared according to Example 6 | 0.08 | 28 | 76 |
| 20a) | Polymer prepared according to Example 7 | 0.02 | 45 | 60 |
| 20b) | Polymer prepared according to Example 7 | 0.04 | 33 | 68 |
| 20c) | Polymer prepared according to Example 7 | 0.06 | 29 | 74 |
| 20d) | Polymer prepared according to Example 7 | 0.08 | 26 | 77 |
| Comparative Example | | | | |
| 23 | — | — | 77 | 30 |
| 24a) | Polymer 1b | 0.02 | 44 | 59 |
| 24b) | " | 0.04 | 34 | 62 |
| 24c) | " | 0.06 | 29 | 74 |
| 24d) | " | 0.08 | 27 | 76 |

Examples 21 to 23

A pulp having a consistency of 2 g/l and a freeness of 50° SR was produced from 33 parts of unprinted newsprint, 33 parts of corrugated board and 33 parts of printed LWC paper. The pH of the pulp was 7. The amounts of polymers stated in each case in Table 10 were added to samples of this paper stock, with the exception of Comparative Example 25, and the drainage times for 600 ml of filtrate were determined in a Schopper-Riegler tester. The optical transmittance of the filtrate was also measured. The results are shown in Table 10.

TABLE 10

| Example | Polymer used | Amount of polymer, based on dry paper stock [%] | Drainage time [sec] | Optical transmittance [%] |
|---|---|---|---|---|
| 21a) | Polymer prepared according to Example 5 | 0.02 | 61 | 44 |
| 21b) | Polymer prepared according to Example 5 | 0.04 | 49 | 56 |

TABLE 10-continued

| Example | Polymer used | Amount of polymer, based on dry paper stock [%] | Drainage time [sec] | Optical transmittance [%] |
|---|---|---|---|---|
| 21c) | Polymer prepared according to Example 5 | 0.06 | 41 | 62 |
| 21d) | Polymer prepared according to Example 5 | 0.08 | 36 | 67 |
| 22a) | Polymer prepared according to Example 6 | 0.02 | 57 | 50 |
| 22b) | Polymer prepared according to Example 6 | 0.04 | 42 | 58 |
| 22c) | Polymer prepared according to Example 6 | 0.06 | 35 | 67 |
| 22d) | Polymer prepared according to Example 6 | 0.08 | 28 | 71 |
| 23a) | Polymer prepared according to Example 7 | 0.02 | 59 | 43 |
| 23b) | Polymer prepared according to Example 7 | 0.04 | 42 | 62 |
| 23c) | Polymer prepared according to Example 7 | 0.06 | 35 | 68 |
| 23d) | Polymer prepared according to Example 7 | 0.08 | 29 | 72 |
| Comparative Example | | | | |
| 25 | — | — | 82 | 27 |
| 26a) | Polymer 1b | 0.02 | 59 | 45 |
| 26b) | " | 0.04 | 43 | 60 |
| 26c) | " | 0.06 | 35 | 67 |
| 26d) | " | 0.08 | 31 | 69 | were determined in a Schopper-Riegler tester for 600 ml of filtrate. The optical transmittance of the filtrates was also measured. The results are shown in Table 11.

TABLE 11

| Example | Polymer used | Amount of polymer, based on dry paper stock [%] | Drainage time [sec] | Optical transmittance [%] |
|---|---|---|---|---|
| 24a) | Polymer prepared according to Example 5 | 0.02 | 82 | 21 |
| 24b) | Polymer prepared according to Example 5 | 0.04 | 74 | 27 |
| 24c) | Polymer prepared according to Example 5 | 0.06 | 69 | 35 |
| 24d) | Polymer prepared according to Example 5 | 0.08 | 62 | 44 |
| 25a) | Polymer prepared according to Example 6 | 0.02 | 82 | 25 |
| 25b) | Polymer prepared according to Example 6 | 0.04 | 69 | 33 |
| 25c) | Polymer prepared according to Example 6 | 0.06 | 52 | 52 |
| 25d) | Polymer prepared according to Example 6 | 0.08 | 42 | 67 |
| 26a) | Polymer prepared according to Example 7 | 0.02 | 84 | 23 |
| 26b) | Polymer prepared according to Example 7 | 0.04 | 70 | 34 |
| 26c) | Polymer prepared according to Example 7 | 0.06 | 56 | 52 |
| 26d) | Polymer prepared according to Example 7 | 0.08 | 50 | 58 |
| Comparative Example | | | | |
| 27 | — | — | 82 | 20 |
| 28a) | Polymer 1b | 0.02 | 75 | 21 |
| 28b) | " | 0.04 | 71 | 27 |
| 28c) | " | 0.06 | 67 | 41 |
| 28d) | " | 0.08 | 56 | 51 |

Examples 24 to 26

A pulp having a consistency of 2 g/l and a freeness of 50° SR was produced from 33 parts of unprinted newsprint, 33 parts of corrugated board and 33 parts of printed LWC paper. The pH of the pulp was 7. 0.2%, based on dry paper stock, of waterglass (solid) was added to this pulp. The amounts of polymer stated in each case in Table 11 were added to samples of this paper stock, with the exception of Comparative Example 27, and the drainage times of these samples Example 27

4 kg of a 20% strength aqueous solution of polymer 1a) were filtered through a hollow fiber cartridge from A/G Technology with a cut-off of 3000, while maintaining the volume on the retentate side by adding 12 kg of water, until the conductivity of the permeate was below 200 mS/cm. 18.2% of the polymer used were present on the retentate side. The permeate was evaporated down to a concentration of 62.5% with the aid of a falling-film evaporator. The starting polymer, retentate and filtrate had the following properties:

| | Viscosity [mPa · s] (10 % strength aqueous solution, pH 10, 20° C.) | $M_w/M_n$ |
|---|---|---|
| Polymer 1a) | 22 | 5.3 |
| Retentate | 36 | 2.7 |
| Permeate | 20 | 4.5 |

600 g of 25% strength aqueous solution of the retentate described above were crosslinked with 55 g of a 20% strength aqueous solution of bisglycidyl ether of a polyethylene glycol of molar mass 1500 at 70° C. in a reactor equipped with a stirrer. A 25.8% strength aqueous solution was obtained. The pH was brought to 7.9 by adding sulfuric acid. A 10% strength aqueous solution had a viscosity of 1170 mPa·s.

Example 28

600 g of 25% strength aqueous solution of the permeate described in Example 27 were initially taken in a reactor equipped with a stirrer and were crosslinked at 70° C. by adding 55 g of a 20% strength aqueous solution of the bisglycidyl ether of the polyethylene glycol having a molar mass of 1500. An aqueous polymer solution having a solids content of 24.9% was obtained. The pH of the solution was brought to 7.8 by adding sulfuric acid. A 10% strength aqueous solution had a viscosity of 950 mPa·s.

Example 29

4.8 kg of a 12.5% strength aqueous solution of polymer 1b were subjected to an ultrafiltration through a hollow fiber cartridge from A/G Technology Corp. having a cut-off of 3000. The volume on the retentate side was maintained by adding water. 11.4 kg of a filtrate (permeate) which had a solids content of 2.4% were obtained. 44% of the polymer were isolated.

Example 30

The retentate from Example 29 was subjected to the ultrafiltration through a hollow fiber cartridge having a cut-off of 10,000, the volume on the retentate side being maintained by adding water. The amount of the filtrate (permeate) was 6.1 kg and the solids content of the permeate was 0.4%. 8% of polymer were isolated.

Example 31

The retentate from Example 30 was subjected to the ultrafiltration in a hollow fiber cartridge having a cut-off of 30,000. The volume on the retentate side was maintained by adding water. 7.1 kg of a filtrate (permeate) having a solids content of 0.5% were obtained. 13% of polymer were isolated.

Example 32

The retentate from Example 31 was subjected to the ultrafiltration through a hollow fiber cartridge having a cut-off of 100,000, while maintaining the volume on the retentate side by adding water. 8.7 kg of filtrate (permeate) having a solids content of 0.7% were obtained. 25% of polymer were isolated.

Example 33

The retentate from Example 32 was subjected to the ultrafiltration through a hollow fiber cartridge having a cut-off of 300,000, while maintaining the volume on the retentate side by adding water. 6 kg of filtrate (permeate) having a solids content of 0.3% were obtained. The amount of the polymer isolated as permeate was 9%.

Example 34

The retentate obtained according to Example 33 was subjected to ultrafiltration through a hollow fiber cartridge having a cut-off of 500,000, while maintaining the volume on the retentate side by adding water. 6.4 kg of filtrate (permeate) which had a solids content of 0.3% were obtained. The amount of the polymer isolated as permeate was 12%.

Example 35

The retentate obtained according to Example 34 was concentrated to a weight of 2.1 kg with a solids content of 7.1% with the aid of continued ultrafiltration through a hollow fiber cartridge having a cut-off of 500,000.

The polymers separated off by ultrafiltration according to Examples 29 to 35 were tested in the following examples as draining aids, retention aids and fixing compositions in papermaking.

Examples 36 and 37

A pulp having a consistency of 2.2 g/l and a freeness of 615 SR was produced from 100 parts of unprinted newsprint having a filler content of about 10% and containing 10 parts of china clay of type X 1 from ECC. The pH of the pulp was 7.5. The amounts of polymers stated in Table 12, based on dry paper stock were added to samples of this paper stock and thoroughly mixed with the paper stock. Immediately thereafter, the drainage times for 600 ml of filtrate in each case were determined in a Schopper-Riegler tester. The results shown in Table 12 were obtained. For comparison, sheet formation was tested without addition of a polymer and with addition of polymer 1b.

TABLE 12

| Example | Polymer used | Amount of polymer, based on dry paper stock [%] | Drainage time [sec] | Optical transmittance of the filtrate [%] |
|---|---|---|---|---|
| 36a) | prepared according to Example 27 | 0.01 | 40 | 72 |
| 36b) | prepared according to Example 27 | 0.02 | 24 | 82 |

TABLE 12-continued

| Example | Polymer used | Amount of polymer, based on dry paper stock [%] | Drainage time [sec] | Optical transmittance of the filtrate [%] |
|---|---|---|---|---|
| 36c) | prepared according to Example 27 | 0.03 | 20 | 87 |
| 36d) | prepared according to Example 27 | 0.04 | 17 | 88 |
| 37a) | prepared according to Example 28 | 0.01 | 44 | 60 |
| 37b) | prepared according to Example 28 | 0.02 | 36 | 70 |
| 37c) | prepared according to Example 28 | 0.03 | 29 | 76 |
| 37d) | prepared according to Example 28 | 0.04 | 25 | 81 |
| Comparative Example | | | | |
| 29 | — | — | 69 | 36 |
| 30a) | Polymer 1b) | 0.01 | 43 | 62 |
| 30b) | Polymer 1b) | 0.02 | 33 | 73 |
| 30c) | Polymer 1b) | 0.03 | 26 | 80 |
| 30d) | Polymer 1b) | 0.04 | 23 | 81 |

Examples 38 to 44

A pulp having a consistency of 2.4 g/l and a freeness of 61° SR was produced from 100 parts of unprinted newsprint having a filler content of about 10% and containing 20 parts of natural chalk of type DX1 from Omya. The pH of the pulp was 7.5. The polymers stated in Table 13 were added in each case to samples of this paper stock and mixed with the paper stock. The mixtures thus obtained were then each drained in a Schopper-Riegler tester. The drainage times for 600 ml of filtrate were determined in each case. The optical transmittance of the filtrate was also measured. The test conditions and results are shown in Table 13.

TABLE 13

| Example | Polymer used | Amount of polymer, based on dry paper stock [%] | Drainage time [sec] | Optical transmittance of the filtrate [%] |
|---|---|---|---|---|
| 38a) | Permeate obtained according to Example 29 | 0.02 | 88 | 11 |
| 38b) | Permeate obtained according to Example 29 | 0.04 | 86 | 11 |
| 38c) | Permeate obtained according to Example 29 | 0.06 | 81 | 15 |
| 38d) | Permeate obtained according to Example 29 | 0.08 | 82 | 15 |
| 39a) | Permeate obtained according to Example 30 | 0.02 | 90 | 12 |
| 39b) | Permeate obtained according to Example 30 | 0.04 | 85 | 14 |
| 39c) | Permeate obtained according to Example 30 | 0.06 | 85 | 16 |
| 39d) | Permeate obtained according to Example 31 | 0.08 | 78 | 21 |
| 40a) | Permeate obtained according to Example 31 | 0.02 | 86 | 14 |
| 40b) | Permeate obtained according to Example 31 | 0.04 | 80 | 20 |
| 40c) | Permeate obtained according to Example 31 | 0.06 | 68 | 26 |

TABLE 13-continued

| Example | Polymer used | Amount of polymer, based on dry paper stock [%] | Drainage time [sec] | Optical transmittance of the filtrate [%] |
|---|---|---|---|---|
| 40d) | Permeate obtained according to Example 31 | 0.08 | 66 | 30 |
| 41a) | Permeate obtained according to Example 32 | 0.02 | 78 | 20 |
| 41b) | Permeate obtained according to Example 32 | 0.04 | 65 | 34 |
| 41c) | Permeate obtained according to Example 32 | 0.06 | 53 | 40 |
| 41d) | Permeate obtained according to Example 32 | 0.08 | 47 | 48 |
| 42a) | Permeate obtained according to Example 33 | 0.02 | 72 | 31 |
| 42b) | Permeate obtained according to Example 33 | 0.04 | 54 | 43 |
| 42c) | Permeate obtained according to Example 33 | 0.06 | 42 | 52 |
| 42d) | Permeate obtained according to Example 33 | 0.08 | 38 | 55 |
| 43a) | Permeate obtained according to Example 34 | 0.02 | 67 | 30 |
| 43b) | Permeat obtained according to Example 34 | 0.04 | 46 | 50 |
| 43c) | Permeate obtained according to Example 34 | 0.06 | 36 | 60 |
| 43d) | Permeate obtained according to Example 34 | 0.08 | 31 | 67 |
| 44a) | Retentate obtained according to Example 35 | 0.02 | 50 | 45 |
| 44b) | Retentate obtained according to Example 35 | 0.04 | 29 | 69 |
| 44c) | Retentate obtained according to Example 35 | 0.06 | 23 | 76 |
| 44d) | Retentate obtained according to Example 35 | 0.08 | 19 | 83 |
| Comparative Example | | | | |
| 31 | — | — | 91 | 11 |
| 32a) | Polymer 1b) | 0.02 | 77 | 20 |
| 32b) | Polymer 1b) | 0.04 | 57 | 43 |
| 32c) | Polymer 1b) | 0.06 | 41 | 53 |
| 32d) | Polymer 1b) | 0.08 | 35 | 60 |

Examples 45 to 51

A pulp having a consistency of 2 g/l was produced from a mixture of 33 parts of unprinted newsprint, 33 parts of corrugated board and 33 parts of printed LWC paper having a freeness of 58° (SR [sic], The pH of the pulp was 7.5. The polymers stated in Table 14 were added to samples of this paper stock and, after mixing, drainage was carried out in each case in a Schopper-Riegler tester. The drainage times for 600 ml of filtrate in each case and the optical transmittance of the filtrate were determined. The results are shown in Table 14, together with the results of comparative examples.

TABLE 14

| Example | Polymer used | Amount of polymer, based on dry paper stock [%] | Drainage time [sec] | Optical transmittance of the filtrate [%] |
|---|---|---|---|---|
| 45a) | Permeate obtained according to Example 29 | 0.02 | 83 | 25 |
| 45b) | Permeate obtained according to Example 29 | 0.04 | 85 | 26 |
| 45c) | Permeate obtained according to Example 29 | 0.06 | 75 | 30 |
| 45d) | Permeat obtained according to Example 29 | 0.08 | 76 | 30 |
| 46a) | Permeat obtained according to Example 30 | 0.02 | 77 | 29 |
| 46b) | Permeat obtained according to Example 30 | 0.04 | 72 | 33 |
| 46c) | Permeate obtained according to Example 30 | 0.06 | 67 | 34 |
| 46d) | Permeate obtained according to Example 30 | 0.08 | 66 | 38 |
| 47a) | Permeate obtained according to Example 31 | 0.02 | 70 | 34 |
| 47b) | Permeate obtained according to Example 31 | 0.04 | 65 | 38 |
| 47c) | Permeate obtained according to Example 31 | 0.06 | 63 | 42 |
| 47d) | Permeate obtained according to Example 31 | 0.08 | 56 | 46 |
| 48a) | Permeate obtained according to Example 32 | 0.02 | 59 | 44 |
| 48b) | Permeate obtained according to Example 32 | 0.04 | 51 | 50 |
| 48c) | Permeate obtained according to Example 32 | 0.06 | 44 | 57 |
| 48d) | Permeate obtained according to Example 32 | 0.08 | 42 | 61 |
| 49a) | Permeate obtained according to Example 33 | 0.02 | 54 | 47 |
| 49b) | Permeate obtained according to Example 33 | 0.04 | 43 | 59 |
| 49c) | Permeate obtained according to Example 33 | 0.06 | 37 | 62 |
| 49d) | Permeate obtained according to Example 33 | 0.08 | 33 | 68 |
| 50a) | Permeate obtained according to Example 34 | 0.02 | 49 | 51 |
| 50b) | Permeate obtained according to Example 34 | 0.04 | 37 | 62 |
| 50c) | Permeate obtained according to Example 34 | 0.06 | 33 | 71 |
| 50d) | Permeate obtained according to Example 34 | 0.08 | 28 | 72 |
| 51a) | Retentate obtained according to Example | 0.02 | 39 | 65 |

TABLE 14-continued

| Example | Polymer used | Amount of polymer, based on dry paper stock [%] | Drainage time [sec] | Optical transmittance of the filtrate [%] |
|---|---|---|---|---|
| 51b) | Retentate obtained according to Example 35 | 0.04 | 25 | 79 |
| 51c) | Retentate obtained according to Example 35 | 0.06 | 19 | 87 |
| 51d) | Retentate obtained according to Example 35 | 0.08 | 16 | 88 |
| Comparative Examples | | | | |
| 33 | — | — | 78 | 25 |
| 34a) | Polymer 1b) | 0.02 | 53 | 48 |
| 34b) | Polymer 1b) | 0.04 | 43 | 61 |
| 34c) | Polymer 1b) | 0.06 | 35 | 67 |
| 34d) | Polymer 1b) | 0.08 | 31 | 73 |

Examples 52–58

An aqueous fiber suspension having a consistency of 2% was produced from TMP (thermomechanical pulp), and an aqueous solution of humic acid was added as an interfering substance. The pulp thus produced served as a test substance. In each case the amounts of polymer stated in Table 15 and additionally in each case the same amount of a cationic polyacrylamide, as a flocculant, were added to samples of this pulp. The samples were shaken and then filtered. In order to evaluate the fixing effect of the polymers stated in Table 15, the extinction of the filtrates obtained in each case was determined. The measured values are shown in Table 15. As is evident therefrom, polymers having a low molar mass are scarcely affected. On the other hand, medium and high molecular weight fractions exhibit in some cases better efficiencies than the comparison polymer 1b). Examples 55, 56 and 58 give a better fixing effect than polymer 1b).

TABLE 15

| Example | Polymer used | Amount of polymer, based on dry paper stock [%] | Extinction of the solution at 588 nm |
|---|---|---|---|
| 52a) | Permeate obtained according to Example 29 | 0.30 | 0.518 |
| 52b) | Permeate obtained according to Example 29 | 0.50 | 0.483 |
| 52c) | Permeate obtained according to Example 29 | 0.80 | 0.478 |
| 52d) | Permeate obtained according to Example 29 | 1.00 | 0.468 |
| 52e) | Permeate obtained according to Example 29 | 1.25 | 0.456 |
| 52f) | Permeate obtained according to Example 29 | 1.50 | 0.443 |
| 53a) | Permeate obtained according to Example 30 | 0.30 | 0.527 |
| 53b) | Permeate obtained according to Example 30 | 0.50 | 0.496 |
| 53c) | Permeate obtained according to Example 30 | 0.80 | 0.460 |
| 53d) | Permeate obtained according to Example 30 | 1.00 | 0.454 |
| 53e) | Permeate obtained according to Example 30 | 1.25 | 0.440 |
| 53f) | Permeate obtained | 1.50 | 0.426 |

TABLE 15-continued

| Example | Polymer used | Amount of polymer, based on dry paper stock [%] | Extinction of the solution at 588 nm |
|---|---|---|---|
| | according to Example 30 | | |
| 54a) | Permeate obtained according to Example 31 | 0.30 | 0.531 |
| 54b) | Permeate obtained according to Example 31 | 0.50 | 0.490 |
| 54c) | Permeate obtained according to Example 31 | 0.80 | 0.469 |
| 54d) | Permeate obtained according to Example 31 | 1.00 | 0.448 |
| 54e) | Permeate obtained according to Example 31 | 1.25 | 0.424 |
| 54f) | Permeate obtained according to Example 31 | 1.50 | 0.418 |
| 55a) | Permeate obtained according to Example 32 | 0.30 | 0.489 |
| 55b) | Permeate obtained according to Example 32 | 0.50 | 0.468 |
| 55c) | Permeate obtained according to Example 32 | 0.80 | 0.415 |
| 55d) | Permeate obtained according to Example 32 | 1.00 | 0.409 |
| 55e) | Permeate obtained according to Example 32 | 1.25 | 0.401 |
| 55f) | Permeate obtained according to Example 32 | 1.50 | 0.393 |
| 56a) | Permeate obtained according to Example 33 | 0.30 | 0.474 |
| 56b) | Permeate obtained according to Example 33 | 0.50 | 0.455 |
| 56c) | Permeate obtained according to Example 33 | 0.80 | 0.429 |
| 56d) | Permeate obtained according to Example 33 | 1.00 | 0.404 |
| 56e) | Permeate obtained according to Example 33 | 1.25 | 0.406 |
| 56f) | Permeate obtained according to Example 33 | 1.50 | 0.406 |
| 57a) | Permeate obtained according to Example 34 | 0.30 | 0.506 |
| 57b) | Permeate obtained according to Example 34 | 0.50 | 0.460 |
| 57c) | Permeate obtained according to Example 34 | 0.80 | 0.433 |
| 57d) | Permeate obtained according to Example 34 | 1.00 | 0.427 |
| 57e) | Permeate obtained according to Example 34 | 1.25 | 0.423 |
| 57f) | Permeate obtained according to Example 34 | 1.50 | 0.420 |

TABLE 15-continued

| Example | Polymer used | Amount of polymer, based on dry paper stock [%] | Extinction of the solution at 588 nm |
|---|---|---|---|
| 58a) | Permeate obtained according to Example 35 | 0.30 | 0.492 |
| 58b) | Permeate obtained according to Example 35 | 0.50 | 0.452 |
| 58c) | Permeate obtained according to Example 35 | 0.80 | 0.422 |
| 58d) | Permeate obtained according to Example 35 | 1.00 | 0.418 |
| 58e) | Permeate obtained according to Example 35 | 1.25 | 0.418 |
| 58f) | Permeate obtained according to Example 35 | 1.50 | 0.416 |
| Comparative Examples | | | |
| 35 | — | — | 0.550 |
| 36a) | Polymer 1 b) | 0.30 | 0.517 |
| 36b) | Polymer 1 b) | 0.50 | 0.498 |
| 36c) | Polymer 1 b) | 0.80 | 0.458 |
| 36d) | Polymer 1 b) | 1.00 | 0.451 |
| 36e) | Polymer 1 b) | 1.25 | 0.432 |
| 36f) | Polymer 1 b) | 1.50 | 0.414 |

Example 59 (polymers 3, 3a, 3b)

10.0 kg of a 10% strength aqueous solution of the commercial polyamine Retaminole® SH (=polymer 3) from Bayer AG, having a charge density of 8.1 meq/g (pH=7), were subjected to diafiltration at a pH of 8.5 and with the addition of 40 kg of water through an ultrafiltration membrane from A/G-Technology having a cut-off of 100,000 until a conductivity of 0.03 mS/cm was reached. The retentate (polymer 3a) was obtained as a 3.8% strength aqueous solution after concentration. A total of 71% by weight of the dissolved starting material were separated off as permeate (polymer 3b).

Example 60 (polymers 4, 4a)

3.4 kg of an 8% strength aqueous solution of the commercial polyamine Cartaretin® I (=polymer 4) from Clariant, having a charge density of 4.9 meq/g at a pH of 7, were subjected to diafiltration at a pH of 7.1 with a total of 17 kg of water through an ultrafiltration membrane from A/G-Technology having a cut-off of 100,000 until a conductivity of 0.09 mS/cm was reached. The retentate (fraction>100,000, polymer 4a) was evaporated down to a concentration of 8.2%. 71% by weight of the dissolved starting material were separated off as permeate (fraction<100,000).

Example 61 (polymers 5, 5a, 5b)

5.0 kg of a 5% strength aqueous solution of the polyamine Catiofast SF (=polymer 5) from BASF, having a charge density of 12.3 meq/g at a pH of 7, were subjected to diafiltration at a pH of 12.1 with a total of 15 kg of water through an ultrafiltration membrane from A/G-Technology having a cut-off of 100,000 until a conductivity of 0.07 mS/cm was reached. (40% by weight of the dissolved starting material are thus separated off as permeate—polymer 5b). After the pH had been brought to 7.5 with formic acid, the retentate—polymer 5a—was concentrated to give a 14.1% strength aqueous solution.

Example 62 (polymers 6, 6a, 6b)

18.1 kg of a 10% strength aqueous solution of the polyamine Catiofast PL (=polymer 6) from BASF, having a charge density of 12.6 meq/g, were subjected to diafiltration at a pH of 11.3 with a total of 24 kg of water through an ultrafiltration membrane from A/G-Technology having a cut-off of 100,000 until a conductivity of 0.16 mS/cm was reached. After 47% by weight of the dissolved starting material had been separated off as permeate—polymer 6b—the retentate (fraction>100,000, polymer 6a) was isolated. Concentration and addition of formic acid to a pH of 7.5 gave a 27.6% strength aqueous solution.

Example 63 and Comparative Example 37

A pulp having a consistency of 5 g/l and a freeness of 58° SR (Schopper-Riegler) was produced from 100 parts of unprinted newsprint having a filler content of about 10% and containing 10 parts of china clay (type XI from ECC). The pH of the pulp was 7.6. The paper stock was divided into several samples, to which the amounts of polymer stated in Table 16 were then added. The drainage time of each sample was determined with 600 ml of filtrate in each case in the Schopper-Riegler tester.

TABLE 16

| Example | Polymer used | Amount of polymer, based on dry paper stock [%] | Extinction of the solution at 588 nm |
|---|---|---|---|
| 63a) | Polymer 3a | 0.02 | 50 |
| 63b) | Polymer 3a | 0.04 | 26 |
| 63c) | Polymer 4a | 0.02 | 71 |

TABLE 16-continued

| Example | Polymer used | Amount of polymer, based on dry paper stock [%] | Extinction of the solution at 588 nm |
|---|---|---|---|
| 63d) | Polymer 4a | 0.04 | 37 |
| 63e) | Retentate of Example 1 | 0.02 | 50 |
| 63f) | Retentate of Example 1 | 0.04 | 29 |
| Comparative Example | | | |
| 37a) | Polymer 1 b | 0.02 | 85 |
| 37b) | Polymer 1 b | 0.04 | 52 |
| 37c) | Polymer 3 | 0.02 | 91 |
| 37e) | Polymer 3 | 0.04 | 68 |
| 37f) | Polymer 4 | 0.02 | 101 |
| 37g) | Polymer 4 | 0.04 | 79 |

Example 64 and Comparative Example 38

A pulp having a consistency of 5 g/l and a freeness of 50° SR was produced from 100 parts of printed newsprint. The pH of the pulp was 7.6. The amounts of polymers stated in Table 17 were added to samples of this paper stock and the drainage time for 600 ml of filtrate in each case was determined in the Schopper-Riegler tester.

TABLE 17

| Example | Polymer used | Amount of polymer, based on dry paper stock [%] | Drainage time [sec] |
|---|---|---|---|
| 64a) | Polymer 3a | 0.02 | 130 |
| 64b) | Polymer 3a | 0.04 | 121 |
| 64c) | Polymer 4a | 0.02 | 122 |
| 64d) | Polymer 4a | 0.04 | 73 |
| 64e) | Retentate of Example 1 | 0.02 | 90 |
| 64f) | Retentate of Example 1 | 0.04 | 47 |
| Comparative Example | | | |
| 38a) | Polymer 1 b | 0.02 | 114 |
| 38b) | Polymer 1 b | 0.04 | 93 |
| 38c) | Polymer 3 | 0.02 | 130 |
| 38d) | Polymer 3 | 0.04 | 121 |
| 38e) | Polymer 4 | 0.02 | 138 |
| 38f) | Polymer 4 | 0.04 | 117 |

Example 65 and Comparative Example 39

A pulp having a consistency of 5 g/l was produced from 50 parts of bleached pine sulfate pulp, 50 parts of bleached beech sulfite pulp and 30 parts of a natural chalk (DX1 from Omya). The pH of the pulp was 7.2. The amounts of polymer stated in Table 18 were [lacuna] to samples of the paper stock, and the drainage times for 600 ml of filtrate were determined in the Schopper-Riegler tester.

TABLE 18

| Example | Polymer used | Amount of polymer, based on dry paper stock [%] | Drainage time [sec] |
|---|---|---|---|
| 65a) | Polymer 3a | 0.02 | 37 |
| 65b) | Polymer 3a | 0.04 | 28 |

TABLE 18-continued

| Example | Polymer used | Amount of polymer, based on dry paper stock [%] | Drainage time [sec] |
|---|---|---|---|
| 65c) | Polymer 4a | 0.02 | 44 |
| 65d) | Polymer 4a | 0.04 | 29 |
| 65e) | Retentate of Example 1 | 0.02 | 35 |
| 65f) | Retentate of Example 1 | 0.04 | 19 |
| Comparative Example | | | |
| 39a) | Polymer 1 b | 0.02 | 41 |
| 39b) | Polymer 1 b | 0.04 | 36 |
| 39c) | Polymer 3 | 0.02 | 54 |
| 39d) | Polymer 3 | 0.04 | 47 |
| 39e) | Polymer 4 | 0.02 | 49 |
| 39f) | Polymer 4 | 0.04 | 47 |

Examples 66–69 and Comparative Examples 40–43

An aqueous fiber suspension of TMP (thermomechanical pulp) having a consistency of 2% was divided into equal portions, and an aqueous solution of wood extract was added, as an interfering substance, to each portion. The amounts, stated in Table 19, of polymer to be tested and additionally the same amount of a cationic polyacrylamide, as a flocculant, were added in each case to samples of this pulp. After thorough mixing and filtration of the flocculated paper stock, the extinction of the alkaline filtrate was determined at 340 nm.

TABLE 19

| Example | Polymer used | Amount of polymer, based on dry paper stock [%] | Extinction of the filtrate [measured at 340 nm] |
|---|---|---|---|
| 66a) | Polymer 5a | 0.30 | 0.467 |
| 66b) | Polymer 5a | 0.50 | 0.403 |
| 66c) | Polymer 5a | 0.80 | 0.374 |
| 66d) | Polymer 5a | 1.00 | 0.321 |
| 66e) | Polymer 5a | 1.25 | 0.303 |
| 66f) | Polymer 5a | 1.50 | 0.263 |
| 67a) | Polymer 6a | 0.30 | 0.425 |
| 67b) | Polymer 6a | 0.50 | 0.336 |
| 67c) | Polymer 6a | 0.80 | 0.312 |
| 67d) | Polymer 6a | 1.00 | 0.282 |
| 67e) | Polymer 6a | 1.25 | 0.246 |
| 67f) | Polymer 6a | 1.50 | 0.235 |
| 68a) | Polymer 3a | 0.30 | 0.480 |
| 68b) | Polymer 3a | 0.50 | 0.435 |
| 68c) | Polymer 3a | 0.80 | 0.312 |
| 68d) | Polymer 3a | 1.00 | 0.393 |
| 68e) | Polymer 3a | 1.25 | 0.344 |
| 68f) | Polymer 3a | 1.50 | 0.356 |
| 69a) | Polymer 4a | 0.30 | 0.479 |
| 69b) | Polymer 4a | 0.50 | 0.444 |
| 69c) | Polymer 4a | 0.80 | 0.404 |
| 69d) | Polymer 4a | 1.00 | 0.396 |
| 69e) | Polymer 4a | 1.25 | 0.362 |
| 69f) | Polymer 4a | 1.50 | 0.344 |
| Comparative Example | | | |
| 40a) | Polymer 5 | 0.30 | 0.483 |
| 40b) | Polymer 5 | 0.50 | 0.422 |
| 40c) | Polymer 5 | 0.80 | 0.388 |
| 40d) | Polymer 5 | 1.00 | 0.361 |
| 40e) | Polymer 5 | 1.25 | 0.350 |

TABLE 19-continued

| Example | Polymer used | Amount of polymer, based on dry paper stock [%] | Extinction of the filtrate [measured at 340 nm] |
|---|---|---|---|
| 40f) | Polymer 5 | 1.50 | 0.316 |
| 41a) | Polymer 6 | 0.30 | 0.429 |
| 41b) | Polymer 6 | 0.50 | 0.383 |
| 41c) | Polymer 6 | 0.80 | 0.347 |
| 41d) | Polymer 6 | 1.00 | 0.336 |
| 41e) | Polymer 6 | 1.25 | 0.323 |
| 41f) | Polymer 6 | 1.50 | 0.271 |
| 42a) | Polymer 3 | 0.30 | 0.479 |
| 42b) | Polymer 3 | 0.50 | 0.460 |
| 42c) | Polymer 3 | 0.80 | 0.451 |
| 42d) | Polymer 3 | 1.00 | 0.438 |
| 42e) | Polymer 3 | 1.25 | 0.404 |
| 42f) | Polymer 3 | 1.50 | 0.398 |
| 43a) | Polymer 4 | 0.30 | 0.529 |
| 43b) | Polymer 4 | 0.50 | 0.491 |
| 43c) | Polymer 4 | 0.80 | 0.471 |
| 43d) | Polymer 4 | 1.00 | 0.464 |
| 43e) | Polymer 4 | 1.25 | 0.440 |
| 43f) | Polymer 4 | 1.50 | 0.420 |

We claim:

1. A process comprising subjecting an aqueous solution of a mixture of water-soluble, amino-containing condensates or adducts having an initial molecular weight distribution to an ultrafiltration through membranes, wherein the condensates or adducts are selected from the group consisting of reaction products of alkylenediamines, polyalkylenepolyamines, ethyleneimine-grafted polyamidoamines and mixtures thereof with crosslinking agents having at least two functional groups, reaction products of Michael adducts of polyalkylene polyamines, polyamidoamines, ethyleneimine-grafted polyamidoamines and mixtures thereof and monoethylenically unsaturated carboxylic acids and salts, esters, amides or nitriles thereof with at least bifunctional crosslinking agents, amidated polyethyleneimines obtained by reaction of polyethyleneimines with monobasic carboxylic acids or their esters, anhydrides, acid chlorides or acid amides and, if required, reaction of the amidated polyethyleneimines with crosslinking agents having at least two functional groups, polyethyleneimines, quaternized polyethyleneimines, phosphonomethylated polyethyleneimines, alkoxylated polyethyleneimines and/or polyethyleneimines carboxymethylated by a Strecker reaction and crosslinked alkoxylated polyethyleneimines, crosslinked, quaternized polyethyleneimines, crosslinked, phosphonomethylated polyethyleneimines and/or crosslinked polyethyleneimines carboxymethylated by a Strecker reaction, to form a lower molecular weight fraction permeate and a higher molecular weight fraction retentate, wherein from 5 to 95% by weight of the condensates or adducts are separated off as the permeate, leaving water-soluble, amino-containing condensates or adducts having a narrower molecular weight distribution than said initial molecular weight distribution in the retentate, and optionally isolating said condensates or adducts from said retentate.

2. The process as claimed in claim 1, wherein from 20 to 90% by weight of the condensates or adducts are separated off as permeate.

3. The process as claimed in claim 1, wherein the ultrafiltration is carried out through membranes having a mean pore diameter of from 0.001 to 10 $\mu$m or through membranes having a cut-off for polymers with molar masses of from 1000 to 10 million.

4. The process as claimed in claim 1, wherein the ultrafiltration is carried out through membranes having a cut-off for polymers with molar masses of from at least 1500 to 500,000.

5. The process as claimed in claim 1, wherein the ultrafiltration is carried out through membranes having a cut-off for polymers with molar masses of at least 100,000.

6. The process as claimed in claim 1, wherein the membranes are used in the form of tubes, hollow fibers, plate-type apparatuses or spiral wound modules.

7. The process as claimed in claim 1, additionally comprising recycling the condensates or adducts which are separated off as permeate to said aqueous solution for further ultrafiltration.

8. The process as claimed in claim 7, additionally comprising, to the condensates or adducts which are separated off as permeate grafting with ethyleneimine or reacting with crosslinking agents having at least two functional groups to give water-soluble, amino-containing condensates or adducts and then subjecting the solutions thus obtainable to the ultrafiltration through membranes, wherein from 5 to 95% by weight of the condensates or adducts are separated off from the solutions as permeate.

9. The process as claimed in any of claim 1, wherein the water-soluble amino-containing condensates used are the reaction products which are obtainable by grafting polyamidoamines with ethyleneimine and then reacting the grafted products with bischlorohydrin ethers or bisglycidyl ethers of polyalkylene glycols as crosslinking agents.

10. The process as claimed in claim 9, wherein the water-soluble amino-containing condensates used are the reaction products which are obtainable by crosslinking ethyleneimine-grafted polyamidoamines with bisglycidyl ethers of polyalkylene glycols which contain from 8 to 100 ethylene oxide and/or propylene oxide units.

11. The process as claimed in any of claim 1, wherein the crosslinking agent used is halogen-free and selected from the group consisting of (1) ethylene carbonate, propylene carbonate or urea, (2) monoethylenically unsaturated carboxylic acids and esters, amides and anhydrides thereof, at least dibasic saturated carboxylic acids or polycarboxylic acids and the esters, amides and anhydrides derived from each of them, (3) reaction products of polyetherdiamines, alkylenediamines, polyalkylenepolyamines, alkylene glycols, polyalkylene glycols or mixtures thereof with monoethylenically unsaturated carboxylic acids, esters, amides or anhydrides of monoethylenically unsaturated carboxylic acids, the reaction products having at least two ethylenically unsaturated double bonds, and carboxamido, carboxyl or ester groups as functional groups, (4) reaction products of dicarboxylic esters with ethyleneimine, which reaction products contain at least two aziridino groups, and mixtures of the stated crosslinking agents.

* * * * *